United States Patent
Ryu et al.

(10) Patent No.: US 11,375,922 B2
(45) Date of Patent: *Jul. 5, 2022

(54) BODY MEASUREMENT DEVICE AND METHOD FOR CONTROLLING THE SAME

(71) Applicant: LG ELECTRONICS INC., Seoul (KR)

(72) Inventors: Eunkyung Ryu, Seoul (KR); Fataliyev Zaur, Seoul (KR); Hyunsu Choi, Seoul (KR); Wonju Lee, Seoul (KR); Hyunchul Choi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 154 days.

This patent is subject to a terminal disclaimer.

(21) Appl. No.: 16/758,798

(22) PCT Filed: Apr. 24, 2019

(86) PCT No.: PCT/KR2019/004949
§ 371 (c)(1),
(2) Date: Apr. 23, 2020

(87) PCT Pub. No.: WO2020/141657
PCT Pub. Date: Jul. 9, 2020

(65) Prior Publication Data
US 2021/0219869 A1 Jul. 22, 2021

Related U.S. Application Data

(60) Provisional application No. 62/787,762, filed on Jan. 3, 2019.

(51) Int. Cl.
*A61B 5/107* (2006.01)
*H04N 5/369* (2011.01)
*G01S 17/894* (2020.01)

(52) U.S. Cl.
CPC .......... *A61B 5/1075* (2013.01); *G01S 17/894* (2020.01); *H04N 5/36965* (2018.08)

(58) Field of Classification Search
CPC ... A61B 5/1075; A61B 5/1079; A61B 5/1073; G01S 17/894; H04N 5/36965
See application file for complete search history.

(56) References Cited

U.S. PATENT DOCUMENTS

| 8,976,230 B1 * | 3/2015 | Vendrow | G06T 11/60 348/46 |
| 10,182,758 B2 * | 1/2019 | Wu | A61B 5/1075 |

(Continued)

FOREIGN PATENT DOCUMENTS

| KR | 10874874 | 12/2008 |
| KR | 1020130081037 | 7/2013 |

(Continued)

OTHER PUBLICATIONS

PCT International Application No. PCT/KR2019/004949, Notification of Transmittal of the International Search Report and the Written Opinion of the International Searching Authority, or Declaration dated Sep. 20, 2019, 10 pages.

*Primary Examiner* — Seung C Sohn
(74) *Attorney, Agent, or Firm* — Lee Hong Degerman Kang & Waimey

(57) ABSTRACT

A body measurement device and a method for controlling the same are disclosed. The body measurement device comprises a TOF camera capturing a first image that includes an RGB image and a depth image; a display displaying a graphic image; and a controller estimating a user's pose based on the first image, controlling the TOF camera to automatically capture a second image, which includes the user's body image in front of the camera, if the user's pose is a first pose, generating the user's body line image based on the captured second image, measuring the (Continued)

user's body size based on the generated body line image; and controlling the display to display the user's body size.

20 Claims, 28 Drawing Sheets

(56) References Cited

U.S. PATENT DOCUMENTS

| | | | |
|---|---|---|---|
| 10,360,444 B2* | 7/2019 | Sugita | G06V 20/64 |
| 10,909,709 B2* | 2/2021 | Ryu | G06T 7/60 |
| 2013/0219434 A1* | 8/2013 | Farrell | H04N 21/4722 |
| | | | 725/60 |

FOREIGN PATENT DOCUMENTS

| | | |
|---|---|---|
| KR | 1020180051727 | 5/2018 |
| KR | 1020180103280 | 9/2018 |
| TW | 201410206 | 3/2014 |

* cited by examiner

RGB  Depth
(a)  (b)

| Height | CHC | UEN | ZF | WJU | PSO | 오차계산(RMSE) | | | RMSE avg |
|---|---|---|---|---|---|---|---|---|---|
| Actual | 1.78 | 1.6 | 1.72 | 1.73 | 1.79 | | | | |
| M-1 | 1.78202 | 1.60991 | 1.7263 | 1.74325 | 1.79694 | 0.002 | 0.010 | 0.006 | 0.013 | 0.007 |
| M-2 | 1.77908 | 1.61356 | 1.72681 | 1.74313 | 1.79634 | -0.001 | 0.014 | 0.007 | 0.013 | 0.006 |
| M-3 | 1.76101 | 1.61339 | 1.72393 | 1.73632 | 1.79752 | -0.019 | 0.013 | 0.004 | 0.006 | 0.008 |
| M-4 | 1.79096 | 1.6109 | 1.72185 | 1.73205 | 1.78233 | 0.011 | 0.011 | 0.002 | 0.002 | -0.008 |
| M-5 | 1.79273 | 1.61307 | 1.72935 | 1.73541 | 1.78466 | 0.013 | 0.013 | 0.009 | 0.005 | -0.005 |
| M-6 | 1.80618 | 1.60023 | 1.72428 | 1.74063 | 1.78558 | 0.026 | 0.000 | 0.004 | 0.011 | -0.004 |
| M-7 | 1.79411 | 1.60968 | 1.73279 | 1.74691 | 1.78769 | 0.014 | 0.010 | 0.013 | 0.017 | -0.002 |
| M-8 | 1.7981 | 1.61075 | 1.72398 | 1.73873 | 1.78805 | 0.018 | 0.011 | 0.004 | 0.009 | -0.002 |
| M-9 | 1.79534 | 1.61064 | 1.7269 | 1.73734 | 1.78826 | 0.015 | 0.011 | 0.007 | 0.007 | -0.002 |
| M-10 | 1.79728 | 1.60886 | 1.72002 | 1.74383 | 1.78551 | 0.017 | 0.009 | 0.000 | 0.014 | -0.004 |
| | | | | | | 0.015 | 0.011 | 0.007 | 0.011 | 0.005 | 0.010 |

FIG. 18

| Bust | CHC | UEN | ZF | WJU | PSO | 오차계산(RMSE) | | | RMSE (AVG) |
|---|---|---|---|---|---|---|---|---|---|
| Actual | 0.98 | 0.89 | 1 | 0.94 | 0.96 | | | | |
| M-1 | 1.04009 | 0.845361 | 1.01695 | 1.03972 | 1.04331 | 0.060 | -0.045 | 0.017 | 0.100 | 0.083 |
| M-2 | 1.02241 | 0.869981 | 1.03189 | 1.04818 | 1.04769 | 0.042 | -0.020 | 0.032 | 0.108 | 0.088 |
| M-3 | 1.00679 | 0.86586 | 1.00939 | 1.07036 | 1.05141 | 0.027 | -0.024 | 0.009 | 0.130 | 0.091 |
| M-4 | 1.01789 | 0.831692 | 1.03495 | 1.04446 | 1.05655 | 0.038 | -0.058 | 0.035 | 0.104 | 0.097 |
| M-5 | 1.01635 | 0.865205 | 0.993069 | 1.04071 | 1.0428 | 0.036 | -0.025 | -0.007 | 0.101 | 0.083 |
| M-6 | 1.00383 | 0.868732 | 1.02785 | 1.02811 | 1.04623 | 0.024 | -0.021 | 0.028 | 0.088 | 0.086 |
| M-7 | 0.994472 | 0.859791 | 1.04227 | 1.02043 | 1.0785 | 0.014 | -0.030 | 0.042 | 0.080 | 0.119 |
| M-8 | 0.986781 | 0.862848 | 0.994109 | 1.02206 | 1.07133 | 0.007 | -0.027 | -0.006 | 0.082 | 0.111 |
| M-9 | 1.00733 | 0.873891 | 1.0031 | 1.01734 | 1.06989 | 0.027 | -0.016 | 0.003 | 0.077 | 0.111 |
| M-10 | 0.980569 | 0.885662 | 1.06355 | 1.04747 | 1.07531 | 0.001 | -0.004 | 0.064 | 0.107 | 0.115 |
| | | | | | | 0.032 | 0.031 | 0.031 | 0.099 | 0.099 |
| | | | | | | | | | | 0.058 |

FIG. 19

| Underbust | CHC | UEN | ZF | WJU | PSO | 오차계산(RMSE) | | | | RMSE (AVG) |
|---|---|---|---|---|---|---|---|---|---|---|
| Actual | 0.88 | 0.76 | 0.92 | 0.81 | 0.87 | | | | | |
| M-1 | 0.959572 | 0.740597 | 0.891556 | 0.845364 | 0.815112 | 0.080 | -0.019 | -0.028 | 0.035 | -0.055 |
| M-2 | 0.960445 | 0.776881 | 0.934841 | 0.837927 | 0.81219 | 0.080 | 0.017 | 0.015 | 0.028 | -0.058 |
| M-3 | 0.885358 | 0.747397 | 0.883519 | 0.83848 | 0.816697 | 0.005 | -0.013 | -0.036 | 0.028 | -0.053 |
| M-4 | 0.869253 | 0.746978 | 0.89718 | 0.848899 | 0.843954 | -0.011 | -0.013 | -0.023 | 0.039 | -0.026 |
| M-5 | 0.903299 | 0.728595 | 0.916648 | 0.835069 | 0.84289 | 0.023 | -0.031 | -0.003 | 0.025 | -0.027 |
| M-6 | 0.854477 | 0.796582 | 0.905937 | 0.842107 | 0.85982 | -0.026 | 0.037 | -0.014 | 0.032 | -0.010 |
| M-7 | 0.889031 | 0.729862 | 0.90858 | 0.888561 | 0.834572 | 0.009 | -0.030 | -0.011 | 0.079 | -0.035 |
| M-8 | 0.842965 | 0.723918 | 0.902044 | 0.887559 | 0.833374 | -0.037 | -0.036 | -0.018 | 0.078 | -0.037 |
| M-9 | 0.895525 | 0.768041 | 0.930673 | 0.881202 | 0.849877 | 0.016 | 0.008 | 0.011 | 0.071 | -0.020 |
| M-10 | 0.880604 | 0.892004 | 0.920384 | 0.910196 | 0.850542 | 0.001 | 0.132 | 0.000 | 0.100 | -0.019 |
| | | | | | | 0.040 | 0.048 | 0.019 | 0.058 | 0.038 | 0.040 |

FIG. 20

| Waist | CHC | UEN | ZF | WJU | PSO | 오차계산(RMSE) | | | RMSE (AVG) |
|---|---|---|---|---|---|---|---|---|---|
| Actual | 0.92 | 0.79 | 0.94 | 0.84 | 0.89 | | | | |
| M-1 | 0.985915 | 0.774177 | 0.984153 | 0.848072 | 0.900526 | 0.066 | -0.016 | 0.044 | -0.002 | 0.011 |
| M-2 | 0.93938 | 0.805008 | 0.98209 | 0.853858 | 0.905829 | 0.019 | 0.015 | 0.042 | 0.014 | 0.016 |
| M-3 | 0.9291 | 0.760689 | 0.985581 | 0.835804 | 0.903069 | 0.009 | -0.029 | 0.046 | -0.004 | 0.013 |
| M-4 | 0.910563 | 0.807643 | 0.992744 | 0.839989 | 0.886952 | -0.009 | 0.018 | 0.053 | 0.000 | -0.003 |
| M-5 | 0.914214 | 0.785268 | 0.978708 | 0.834117 | 0.882578 | -0.006 | -0.005 | 0.039 | -0.006 | -0.007 |
| M-6 | 0.94594 | 0.787401 | 0.981236 | 0.832429 | 0.892524 | 0.026 | -0.003 | 0.041 | -0.008 | 0.003 |
| M-7 | 0.937745 | 0.798734 | 0.956084 | 0.86407 | 0.894294 | 0.018 | 0.009 | 0.016 | 0.024 | 0.004 |
| M-8 | 0.923961 | 0.796514 | 0.956574 | 0.857371 | 0.890259 | 0.004 | 0.007 | 0.017 | 0.017 | 0.000 |
| M-9 | 0.935742 | 0.814224 | 0.959674 | 0.865305 | 0.888368 | 0.016 | 0.024 | 0.020 | 0.025 | -0.002 |
| M-10 | 0.915117 | 0.801508 | 0.965981 | 0.873676 | 0.893012 | -0.005 | 0.012 | 0.026 | 0.034 | 0.003 |
| | | | | | | 0.025 | 0.016 | 0.037 | 0.017 | 0.008 |
| | | | | | | | | | | 0.020 |

FIG. 21

| Hp | CHC | UEN | ZF | WJU | PSO | | 오차계산(RMSE) | | | RMSE (AVG) |
|---|---|---|---|---|---|---|---|---|---|---|
| Actual | 0.99 | 0.94 | 1.02 | 0.95 | 1.01 | | | | | |
| M-1 | 1.09757 | 0.944828 | 1.04016 | 0.980336 | 1.03129 | 0.108 | 0.005 | 0.020 | 0.030 | 0.021 |
| M-2 | 1.06528 | 0.945188 | 1.05617 | 1.01488 | 1.03306 | -0.032 | 0.000 | 0.016 | 0.035 | 0.002 |
| M-3 | 1.0606 | 0.956096 | 1.05953 | 0.976487 | 1.03951 | -0.005 | 0.011 | 0.003 | -0.038 | 0.006 |
| M-4 | 1.04748 | 0.95976 | 1.0458 | 1.0016 | 1.02733 | -0.013 | 0.004 | -0.014 | 0.025 | -0.012 |
| M-5 | 1.04226 | 0.9746 | 1.03926 | 0.987885 | 1.03579 | -0.005 | 0.015 | -0.007 | -0.014 | 0.008 |
| M-6 | 1.0607 | 0.968973 | 1.00894 | 0.982493 | 1.03653 | 0.018 | -0.006 | -0.030 | -0.005 | 0.001 |
| M-7 | 1.05899 | 0.951048 | 1.0308 | 0.987858 | 1.04057 | -0.002 | -0.018 | 0.022 | 0.005 | 0.004 |
| M-8 | 1.0321 | 0.961209 | 1.00953 | 0.991284 | 1.04747 | -0.027 | 0.010 | -0.021 | 0.003 | 0.007 |
| M-9 | 1.05634 | 0.9737 | 1.01427 | 1.0077 | 1.04038 | 0.024 | 0.012 | 0.005 | 0.016 | -0.007 |
| M-10 | 1.03009 | 0.966849 | 1.00704 | 1.02772 | 1.03339 | -0.026 | -0.007 | -0.007 | 0.020 | -0.007 |
| | | | | | | 0.039 | 0.010 | 0.017 | 0.023 | 0.009 | 0.019606 |

FIG. 22

| error | | | | |
|---|---|---|---|---|
| height | Bust circumference | Underbust circumference | Waist circumference | Hip circumference |
| 0.6% | 6.1% | 4.9% | 2.3% | 2.0% |

| accuracy | | | | |
|---|---|---|---|---|
| height | Bust circumference | Underbust circumference | Waist circumference | Hip circumference |
| 99.4% | 93.9% | 95.1% | 97.7% | 98.0% |

FIG. 23

| (Unit : m) | | Error calculation (RMSE) | | | Error calculation (RMSE) | | | error % | | |
|---|---|---|---|---|---|---|---|---|---|---|
| | | Height (length) | Shoulder (length) | Arm (length) | Height (length) | Shoulder (length) | Arm (length) | Height (length) | Shoulder (length) | Arm (length) |
| UEK | Actual | 1.53 | 0.25 | 0.45 | | | | | | |
| | M-1 | 1.52192 | 0.263726 | 0.450191 | 0.00808 | -0.013726 | -0.000191 | | | |
| | M-2 | 1.5304 | 0.26052 | 0.409399 | -0.0004 | -0.01052 | 0.040601 | | | |
| | M-3 | 1.54128 | 0.261508 | 0.405022 | -0.01128 | -0.011508 | 0.044978 | | | |
| | M-4 | 1.53899 | 0.263121 | 0.401977 | -0.00899 | -0.013121 | 0.048023 | | | |
| | M-5 | 1.54272 | 0.271234 | 0.392656 | -0.01272 | -0.021234 | 0.057344 | | | |
| | | | | | 0.00933063 | 0.014522747 | 0.043048905 | 0.006098 | 0.058091 | 0.095664 |
| KBR | Actual | 1.70 | .29 | .52 | | | | | | |
| | M-1 | 1.67122 | 0.29359 | 0.509667 | -0.14122 | -0.04359 | -0.059667 | | | |
| | M-2 | 1.68491 | 0.297406 | 0.52487 | -0.15491 | -0.047406 | -0.07487 | | | |
| | M-3 | 1.66735 | 0.276732 | 0.510197 | -0.13735 | -0.026732 | -0.060197 | | | |
| | M-4 | 1.66946 | 0.281289 | 0.520682 | -0.13946 | -0.031289 | -0.070682 | | | |
| | M-5 | 1.67104 | 0.278205 | 0.494652 | -0.14104 | -0.028205 | -0.044652 | | | |
| | | | | | 0.130533299 | 0.03378227 | 0.060044846 | 0.000768 | 0.001165 | 0.001155 |
| ZU | Actual | 1.71 | .35 | .53 | | | | | | |
| | M-1 | 1.7246 | 0.322574 | 0.515448 | -0.1946 | -0.072574 | -0.065448 | | | |
| | M-2 | 1.71922 | 0.32928 | 0.527736 | -0.18922 | -0.07928 | -0.077736 | | | |
| | M-3 | 1.72439 | 0.327158 | 0.511569 | -0.19439 | -0.077158 | -0.061569 | | | |
| | M-4 | 1.72074 | 0.317665 | 0.505691 | -0.19074 | -0.067665 | -0.055691 | | | |
| | M-5 | 1.72381 | 0.320562 | 0.49197 | -0.19381 | -0.070562 | -0.04197 | | | |
| | | | | | 0.183686257 | 0.068561956 | 0.061353375 | 0.001074 | 0.001959 | 0.001158 |
| CHC | Actual | 1.77 | .33 | .54 | | | | | | |
| | M-1 | 1.7686 | 0.311777 | 0.560264 | -0.2386 | -0.061777 | -0.110264 | | | |
| | M-2 | 1.79259 | 0.310986 | 0.541326 | -0.26259 | -0.060986 | -0.091326 | | | |
| | M-3 | 1.7898 | 0.314044 | 0.516528 | -0.2598 | -0.064044 | -0.066528 | | | |
| | M-4 | 1.78484 | 0.328276 | 0.538383 | -0.25484 | -0.078276 | -0.088383 | | | |
| | M-5 | 1.79116 | 0.315896 | 0.521153 | -0.26116 | -0.065896 | -0.071153 | | | |
| | | | | | 0.245040174 | 0.066842452 | 0.083229706 | 0.001384 | 0.002026 | 0.001541 |
| | | | | | | | % avg | 0.2% | 1.6% | 2.5% |

| error | | |
|---|---|---|
| Height (length) | Shoulder (length) | Arm (length) |
| 0.2% | 1.6% | 2.5% |

| accuracy | | |
|---|---|---|
| Height (length) | Shoulder (length) | Arm (length) |
| 99.8% | 98.4% | 97.5% |

FIG. 25
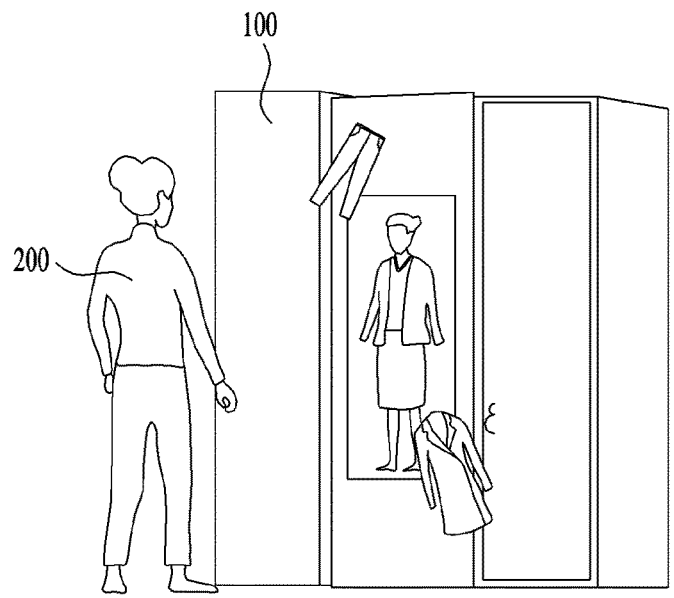
(a)
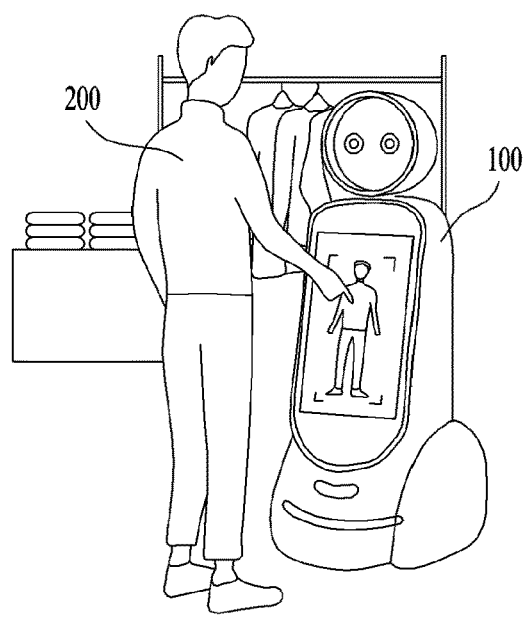
(b)

FIG. 26
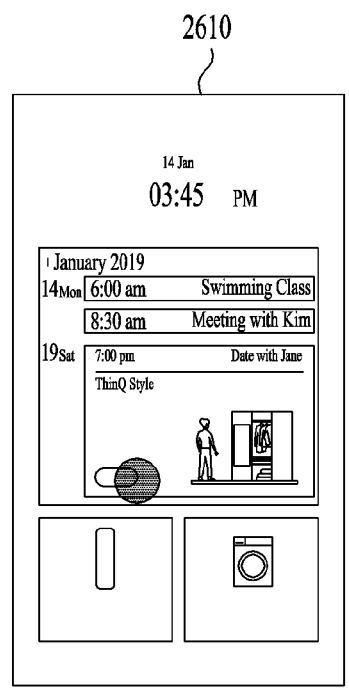
(a)
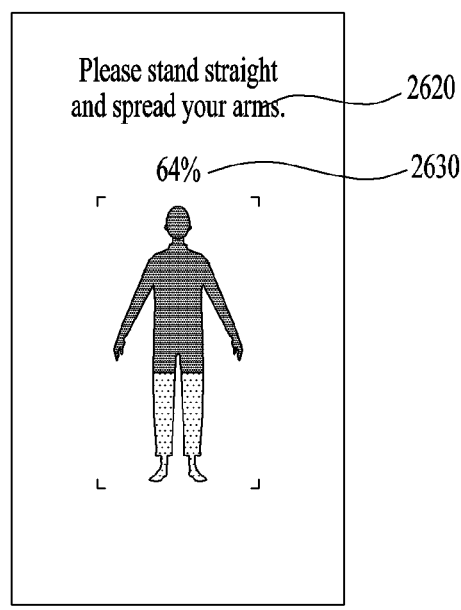
(b)

BODY MEASUREMENT DEVICE AND METHOD FOR CONTROLLING THE SAME

CROSS-REFERENCE TO RELATED APPLICATIONS

This application is the National Stage filing under 35 U.S.C. 371 of International Application No. PCT/KR2019/004949, filed on Apr. 24, 2019, which claims the benefit of U.S. Provisional Application No. 62/787,762, filed on Jan. 3, 2019, the contents of which are all hereby incorporated by reference herein in their entirety.

BACKGROUND OF THE INVENTION

Field of the Invention

The present disclosure relates to a body measurement device and a method for controlling the same, and more particularly, to a body measurement device and a method for controlling the same, in which a user's image is captured, the user's body line image and skeleton image are generated based on the captured image, and the user's body size is measured based on the generated body line image and skeleton image when the user takes a specific pose.

Discussion of the Related Art

Recently, consumers are likely to purchase clothes through online such as Internet shopping mall and home shopping, and a scale of the Internet shopping mall and home shopping has been rapidly increased in accordance with the development of smartphone and network. However, most of consumers do not know their body size exactly. Although the consumers know an approximate body size, for example, 95, 100, 105, 55, 66 and 77, they are not likely to exactly know a bust circumference, a waist circumference, a hip circumference, an arm length, etc.

A consumer should know his/her exact body size per body to select clothes of a desired fit or bust and length suitable for his/her, and may reduce the time required for return and exchange.

In purchasing clothes, size selection is one of the most important factors, and is a factor that causes a considerable concern of a consumer. Moreover, importance and concern of size selection is more increased in purchase on online without actually viewing clothes. Nonetheless, consumers little measure their body size by directly using a tape measure, and even if they do so, it is difficult to obtain an exact value due to a wrong position and method in measurement.

Technologies commercialized among technologies developed to solve the problem are to use a 3D scanner or measure a body size by setting a plurality of digital cameras. However, these technologies have problems in that a specific place and an expensive equipment are required to allow consumers to be difficult to use the technologies.

SUMMARY OF THE INVENTION

Accordingly, the present disclosure is directed to a body measurement device and a method for controlling the same, which substantially obviate one or more problems due to limitations and disadvantages of the related art.

An object of the present disclosure is to provide a body measurement device and a method for controlling the same, in which a user's image is captured, the user's body line image are generated based on the captured image by combining RGB image with depth image, and the user's body size is measured based on the generated body line image when the user takes a specific pose.

Another object of the present disclosure is to provide a body measurement device and a method for controlling the same, in which a skeleton image is extracted from a captured image and a user's pose is estimated based on the skeleton image.

Other object of the present disclosure is to provide a body measurement device and a method for controlling the same, in which a body length is extracted from a body line image and a skeleton image, and a rear waist circumference length is determined by multiplying a specific parameter by a body length.

In addition to the objects of the present disclosure as mentioned above, additional objects and features of the present disclosure will be clearly understood by those skilled in the art from the following description of the present disclosure.

To achieve these objects and other advantages and in accordance with the purpose of the invention, as embodied and broadly described herein, a body measurement device according to one embodiment of the present disclosure comprises a TOF camera capturing a first image that includes an RGB image and a depth image; a display displaying a graphic image; and a controller estimating a user's pose based on the first image, controlling the TOF camera to automatically capture a second image, which includes the user's body image in front of the camera, if the user's pose is a first pose, generating the user's body line image based on the captured second image, measuring the user's body size based on the generated body line image; and controlling the display to display the user's body size.

A method for controlling a body measurement device according to another embodiment of the present disclosure comprises capturing a first image that includes an RGB image and a depth image, through a TOF camera; estimating a user's pose based on the first image; controlling the TOF camera to capture a second image, which includes the user's body image in front of the camera, if the user's pose is a first pose; generating the user's body line image based on the captured second image; measuring the user's body size based on the generated body line image; and controlling a display to display the user's body size.

According to one embodiment of the present disclosure, if the user takes a specific pose, the user's image is captured, and the user's body line image and skeleton image are generated from the captured image. Since the user's body size may be measured based on the generated body line image, the user's image may be captured by a simple operation and an exact body size may be measured, whereby user convenience may be improved.

According to another embodiment of the present disclosure, a skeleton image is extracted from the captured image, and the skeleton image, an RGB image and a depth image may be combined with one another to generate the user's body line image. Therefore, the user's body size may be measured more exactly, whereby user convenience may be improved.

According to still another embodiment of the present disclosure, a first length may be extracted from a body line image, and a specific parameter may be multiplied by the first length to determine a rear waist circumference length. Therefore, a waist circumference length which is invisible from a front image may exactly be measured, whereby user convenience may be improved.

In addition to the effects of the present disclosure as mentioned above, additional effects and features of the present disclosure will be clearly understood by those skilled in the art from the following description of the present disclosure.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 17 illustrates data of a user's actual height and a measured height according to one embodiment of the present disclosure;

FIG. 18 illustrates data of a user's actual bust circumference length and a measured bust circumference length according to one embodiment of the present disclosure;

FIG. 19 illustrates data of a user's actual underbust circumference length and a measured underbust circumference length according to one embodiment of the present disclosure;

FIG. 20 illustrates data of a user's actual waist circumference length and a measured waist circumference length according to one embodiment of the present disclosure;

FIG. 21 illustrates data of a user's actual hip circumference length and a measured hip circumference length according to one embodiment of the present disclosure;

FIG. 22 illustrates data of an error and exactness of a user's body size measurement data according to one embodiment of the present disclosure;

FIG. 23 illustrates data of an error and exactness of a user's body size measurement data according to one embodiment of the present disclosure;

FIG. 25 illustrates a use example of a body measurement device according to one embodiment of the present disclosure;

FIG. 26 illustrates an execution screen of a body measurement device according to one embodiment of the present disclosure;

DETAILED DESCRIPTION OF THE INVENTION

Reference will now be made in detail to the preferred embodiments of the present specification, examples of which are illustrated in the accompanying drawings. Wherever possible, the same reference numbers will be used throughout the drawings to refer to the same or like parts. The suffixes "module" and "unit" for the elements used in the following description are given or used in common by considering facilitation in writing this disclosure only but fail to have meanings or roles discriminated from each other.

Also, in description of the embodiments disclosed in this specification, if detailed description of the disclosure known in respect of the present disclosure is determined to make the subject matter of the embodiments disclosed in this specification obscure, the detailed description will be omitted.

Also, the accompanying drawings are only intended to facilitate understanding of the embodiments disclosed in this specification, and it is to be understood that technical spirits disclosed in this specification are not limited by the accompanying drawings and the accompanying drawings include all modifications, equivalents or replacements included in technical spirits and technical scope of the present disclosure.

Although the terms such as "first" and/or "second" in this specification may be used to describe various elements, it is to be understood that the elements are not limited by such terms. The terms may be used to identify one element from another element.

The expression that an element is "connected" or "coupled" to another element should be understood that the element may directly be connected or coupled to another element, a third element may be interposed between the corresponding elements, or the corresponding elements may be connected or coupled to each other through a third element. On the other hand, the expression that an element is "directly connected" or "directly coupled" to another element" means that no third element exists there between.

It is to be understood that the singular expression used in this specification includes the plural expression unless defined differently on the context.

In this application, it is to be understood that the terms such as "include" and "has" are intended to designate that features, numbers, steps, operations, elements, parts, or their combination, which are disclosed in the specification, exist, and are intended not to previously exclude the presence or optional possibility of one or more other features, numbers, steps, operations, elements, parts, or their combinations.

Figure 1:
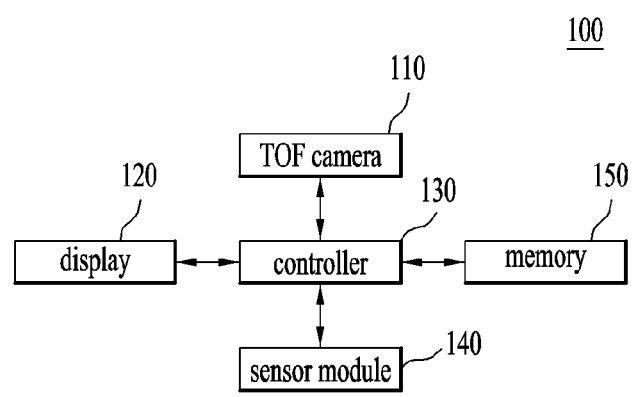
FIG. 1 is a schematic view illustrating a body measurement device according to one embodiment of the present disclosure.

FIG. 1 is a schematic view illustrating a body measurement device according to one embodiment of the present disclosure.

Referring to FIG. 1, the body measurement device 100 includes a TOF camera 110, a display 120, a controller 130, a sensor module 140, and a memory 150.

The TOF camera 110 captures a first image that includes an RGB image and a depth image. The TOF camera 110 refers to a camera having a TOF sensor attached to a general camera. Specifically, an image sensor that captures a scene derives a 2D based result. In addition, TOF sensors can be used to create depth measurements while enabling 3D output. Time of Flight (TOF) is the time to transmit sound waves or light sources to a subject and then return through the subject. TOF sensors are a type of component that can detect this role.

The depth image means an image that includes a depth map. The depth map means an image having information related to a distance from a viewpoint to an object surface in a 3D computer graphic.

The display 120 displays a graphic image in accordance with a control command from the controller 130.

The controller 130 estimates a user's pose based on a first image, and if the user's pose is a first pose, the controller 130 controls the camera 110 to capture a second image that includes a user's body image in front of the camera 110, generates the user's body line image based on the captured second image, measures the user's body size based on the generated body line size, and controls the display 120 to display the user's body size.

The sensor module 140 senses a distance with a user in accordance with the control command from the controller 130.

The memory 150 stores the first image and the second image in accordance with the control command from the controller 130.

Figure 2:
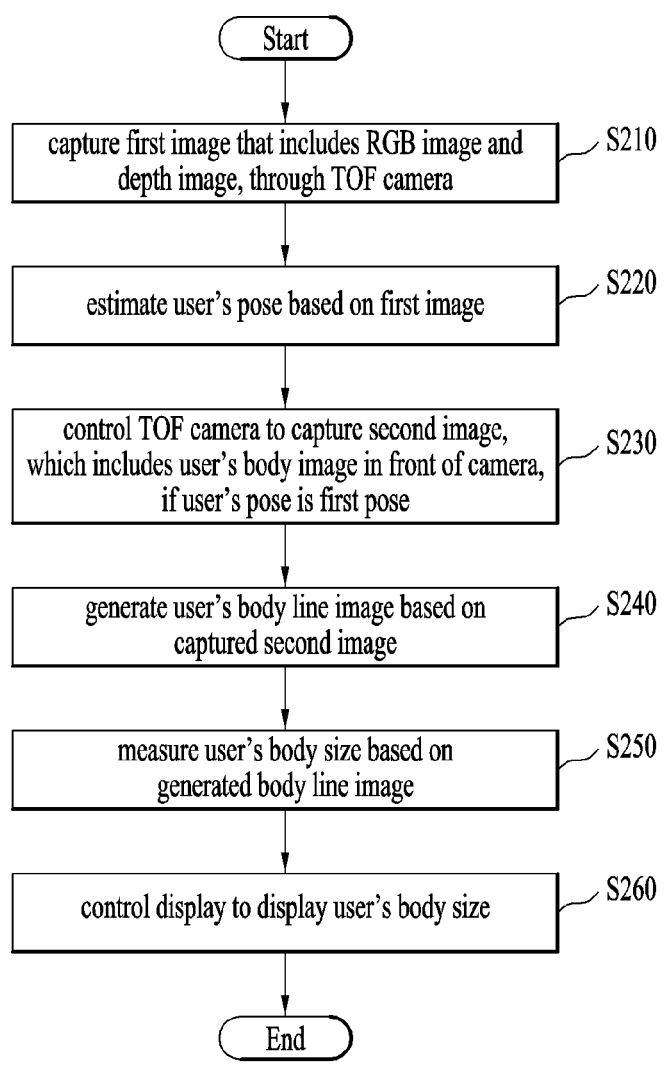
FIG. 2 is a flow chart illustrating a method for controlling a body measurement device according to one embodiment of the present disclosure.

FIG. 2 is a flow chart illustrating a method for controlling a body measurement device according to one embodiment of the present disclosure.

Referring to FIG. 2, a first image that includes an RGB image and a depth image is captured through the TOF camera 110 (S210).

A user's pose is estimated based on the first image (S220).

If the user's pose is a first pose, the TOF camera 110 is controlled to capture a second image that includes the user's body image in front of the camera 110 (S230).

The user's body line image is generated based on the captured second image (S240). According to one embodiment of the present disclosure, the controller 130 extracts a skeleton image based on the first image.

The user's body size is measured based on the generated body line image (S250). Also, the controller 130 may measure a body size based on the body line image and the skeleton image.

The controller 130 controls the display 120 to display the user's body size (S260).

Figure 3:
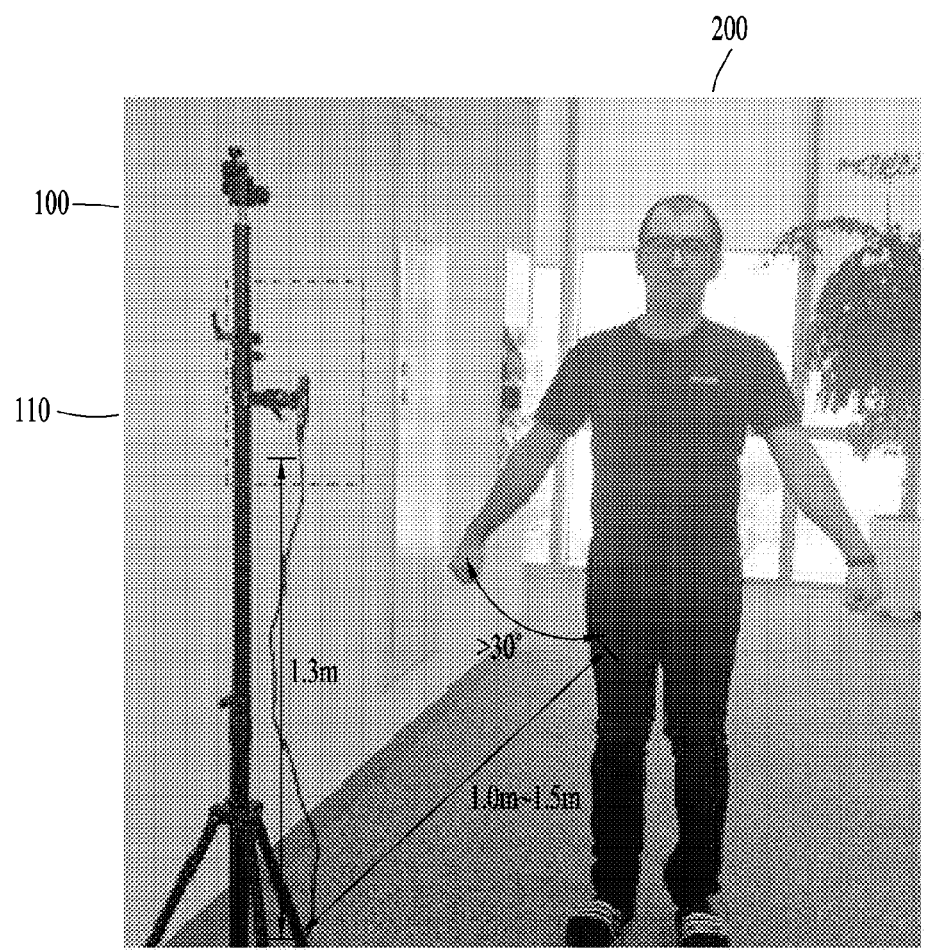
FIG. 3 illustrates that a user stands in front of a body measurement device according to one embodiment of the present disclosure.

FIG. 3 illustrates that a user stands in front of a body measurement device according to one embodiment of the present disclosure.

Referring to FIG. 3, a user 200 stands in front of the body measurement device 100. In this case, the camera 110 includes a TOF camera.

First of all, a position of the camera 110 will be described.

Since the user's leg portion is not captured by the camera 110, it is set to a fixed value to measure the user's height. The position of the camera 110 is changed depending on a range (140 cm to 200 cm in case of height) of a range to be measured. A distance between the camera 110 and the user 200 is determined considering a size of a target to be measured and a field of view (FOV) of the camera 110. The distance is determined considering exactness of a distance value of the depth camera 110. That is, it is important to select a position having high exactness, and exactness of a depth is reduced when the distance between the camera 110 and the user 200 is too short or long.

The position of the camera 110 may be 1.3 m from the ground.

The distance between the camera 110 and the user may range from 1.0 m to 1.5 m.

Resolution of the camera 110 will be described. The higher resolution of the camera 110 is, the higher exactness of a meter per pixel (MPP) is, whereby measurement may be performed more exactly.

An input image of the camera 110 will be described.

The input image may be i) a depth image, ii) a depth image and a RGB image, or iii) a depth image and an IR image.

In case of the depth image, the controller 130 may acquire distance and length information for body measurement from the depth image. If there are no additional RGB image and IR raw image, the controller 130 may extract a skeleton image from the depth image.

In case of the RGB image and the IR raw image, the controller 130 extracts a pose for automatic capturing from the RGB image and the IR raw image.

Also, the RGB image and the IR raw image may be used for additional application. For example, the controller 130 may execute gender recognition through face recognition, weight prediction through deep-learning or weight prediction algorithm and rear circumference prediction (when the user's front image is only captured) through deep-learning, based on the RGB image and the IR raw image.

Also, the controller 130 may improve exactness by executing a fusion algorithm based on information obtained from the depth camera and information using deep-learning having an RGB image and an IR-raw image as inputs.

Figure 4:
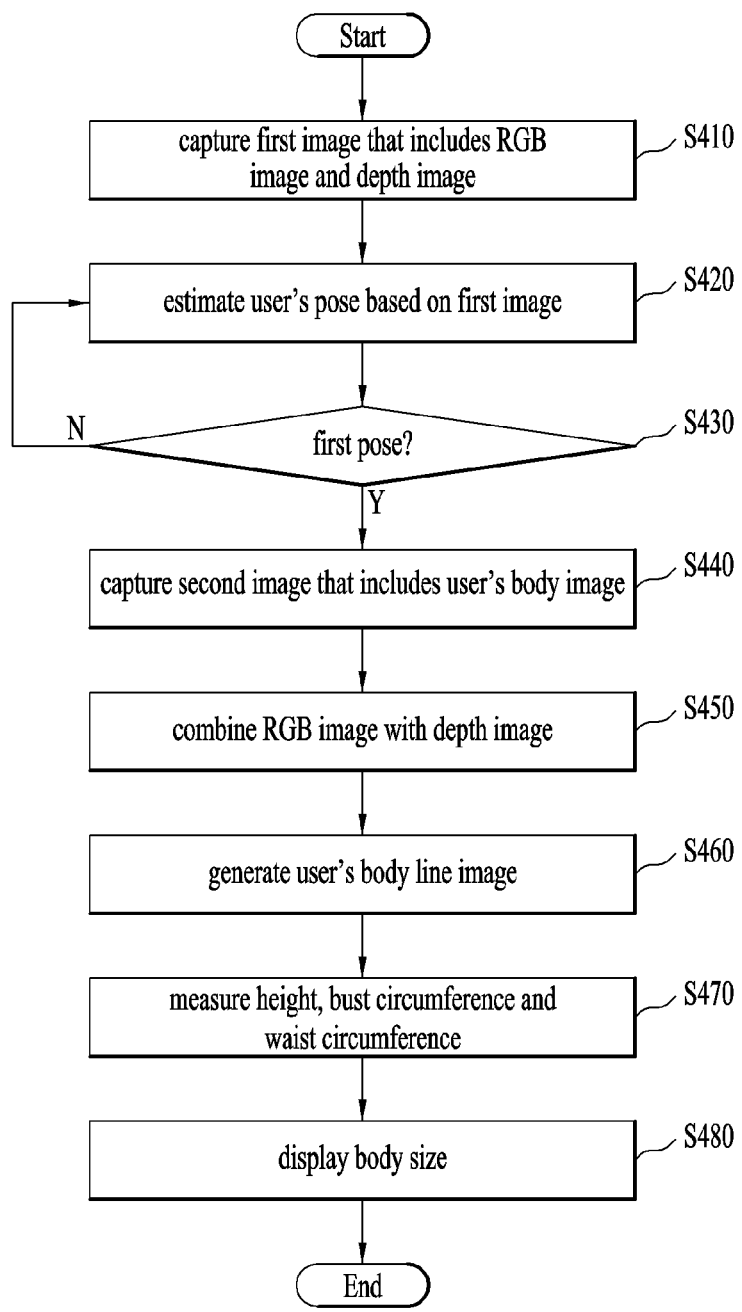
FIG. 4 is a flow chart illustrating a method for controlling a body measurement device according to one embodiment of the present disclosure.

FIG. 4 is a flow chart illustrating a method for controlling a body measurement device according to one embodiment of the present disclosure. The present disclosure is performed by the controller 130.

Referring to FIG. 4, a first image that includes a depth image and an RGB image is captured (S410).

A user's pose is estimated based on the first image (S420).

If the user's pose is a first pose (S430), the camera 110 captures a second image that includes the user's body image (S440). The controller 130 controls the camera 110 to capture an image or continuously capture images. In this case, the first pose may be one pose or a plurality of poses. If the first pose becomes a plurality of poses, it is advantageous that measurement exactness in a body size may be improved.

If the user's pose is not a first pose (S440), the user's pose is again estimated based on the first image (S420). The controller 130 measures a slope corresponding to the user's pose through the sensor module 140, and if the user's pose is more inclined than the first pose toward a left or right direction at a predetermined range or more, the controller 130 displays a warning message on the screen. The controller 130 may control a speaker (not shown) to output a voice message "a pose is inclined toward a right side. So, please stand straight".

According to the present disclosure, if the user's pose is more inclined than the first pose, the warning message is displayed to allow the user to take a right pose, whereby an exact body size may be measured.

The RGB image and the depth image are combined with each other (S450).

The body line image is generated based on the RGB image and the depth image (S460). According to one embodiment of the present disclosure, the controller 130 may generate a body line image and a skeleton image based on the RGB image and the depth image.

A height, a bust circumference, and a waist circumference are measured based on the body line image (S470).

The measured body size is displayed (S480).

Figure 5:
FIG. 5 illustrates input images according to one embodiment of the present disclosure.

FIG. 5 illustrates input images according to one embodiment of the present disclosure. FIG. 5 includes FIG. 5(a) and FIG. 5(b).

FIG. 5(a) means the RGB image of the input images.

The RGB image means an image to which an RGB mode is applied. The RGB model is the most basic color model, and considers a color as a combination of three components of red, green and blue. In the RGB model, a black color is expressed as R=G=B=0, a white color is expressed as R=G=B=255, a red color is expressed as R=255, G=B=0, and a yellow color is expressed as R=G=255, B=0. A case of R=G=B corresponds to a gray color which is an achromatic color.

Since each of R, G and B may have a value between 0 and 255, if the RGB model is used, a total of 256×256×256=16,777,216 colors may be expressed.

FIG. 5(b) means a depth image of the input images.

The depth image means an image obtained by capturing same scenes at different angles to generate a depth map. The depth map means an image indicating a relative distance of pixels existing in the image by categorizing the relative distance in a gray scale. In case of the depth map, a close portion is indicated by bright pixels, and a remote portion is indicated by dark pixels.

Figure 6:
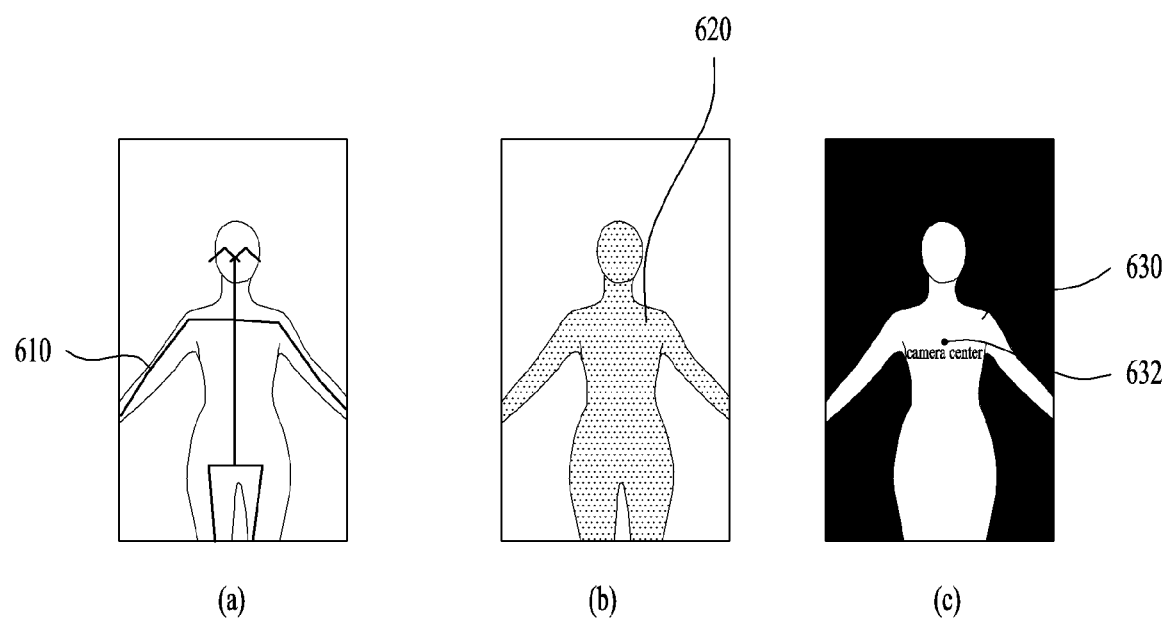
FIG. 6 illustrates that a body line image is generated in accordance with one embodiment of the present disclosure.

FIG. 6 illustrates that a body line image is generated in accordance with one embodiment of the present disclosure. FIG. 6 includes FIG. 6(a), FIG. 6(b), and FIG. 6(c).

FIG. 6(a) illustrates a skeleton image extracted from a second image. FIG. 6(b) illustrates an image obtained by combining an RGB image and a depth image. FIG. 6(c) illustrates a user's body line image.

Referring to FIG. 6(a), the controller 130 extracts a skeleton image 610 based on the second image.

Referring to FIG. 6(b), the controller 130 generates a combined image 620 by combining the RGB image with the depth image.

Referring to FIG. 6(c), the controller 130 generates the user's body line image 630 by combining the extracted skeleton image 610, the RGB image and the depth image 620 with one another.

The controller 130 measures the user's height based on a camera center 632. A detailed description of this case will be given with reference to FIG. 13.

Figure 7:
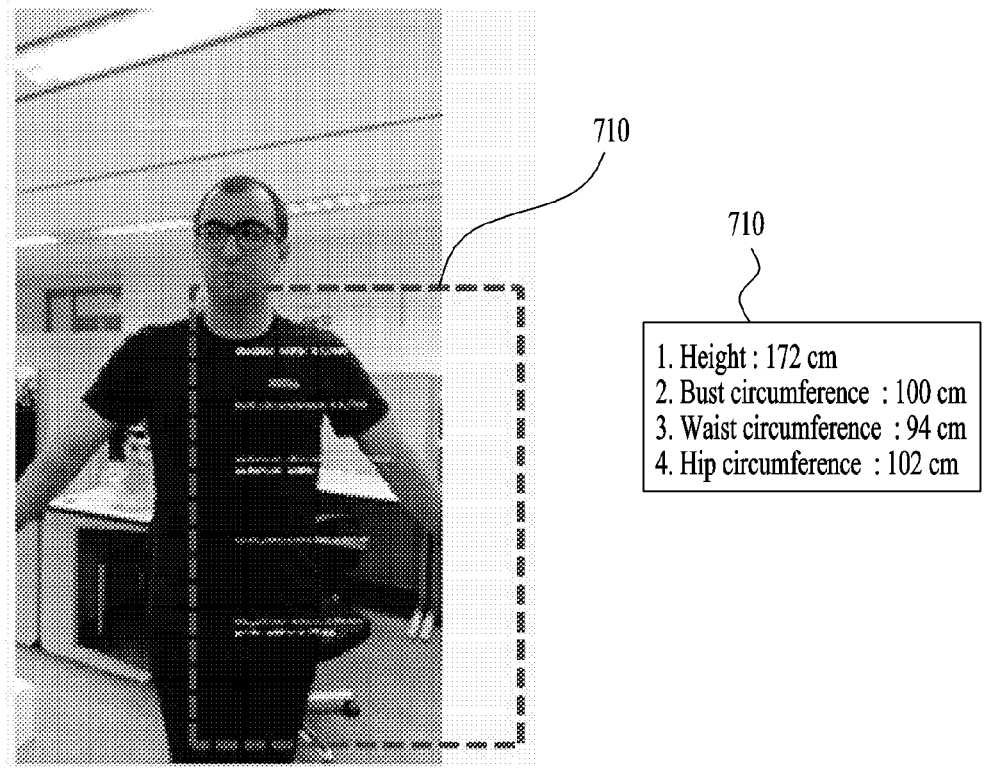
FIG. 7 illustrates that a user's body size measurement result according to one embodiment of the present disclosure.

FIG. 7 illustrates that a user's body size measurement result according to one embodiment of the present disclosure.

Referring to FIG. 7, the controller displays the user's body size measurement result on the screen.

Specifically, the controller 130 displays the user's body size measurement result 710 on the screen.

For example, the body size measurement result includes a height 71, a bust circumference 72, a waist circumference 73, a hip circumference 74. The height 71 may be 172 cm, the bust circumference 72 may be 100 cm, the waist circumference 73 may be 94 cm, and the hip circumference may be 102 cm.

Figure 8:
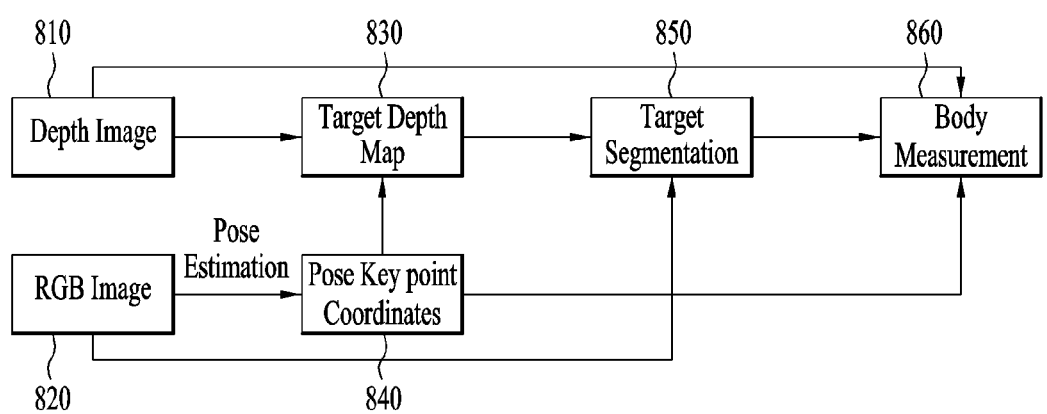
FIG. 8 illustrates a body measurement algorithm according to one embodiment of the present disclosure.

FIG. 8 illustrates a body measurement algorithm according to one embodiment of the present disclosure.

Referring to FIG. 8, a depth image 810 and an RGB image 820 are received as input images.

The controller 130 estimates the user's pose based on the RGB image 820, and generates a pose key point coordinate 840.

The controller 130 generates a target depth map 830 based on the depth image 810 and the pose key point coordinate 840.

The controller 130 generates a target segmentation image 850 based on the target depth map 830 and the RGB image 820.

The controller 130 executes body size measurement 860 based on the target segmentation image 850.

The controller 130 may measure a height, a bust circumference length, an underbust circumference length, a waist circumference length, and a hip circumference length as body size measurement of a target.

Figure 9:
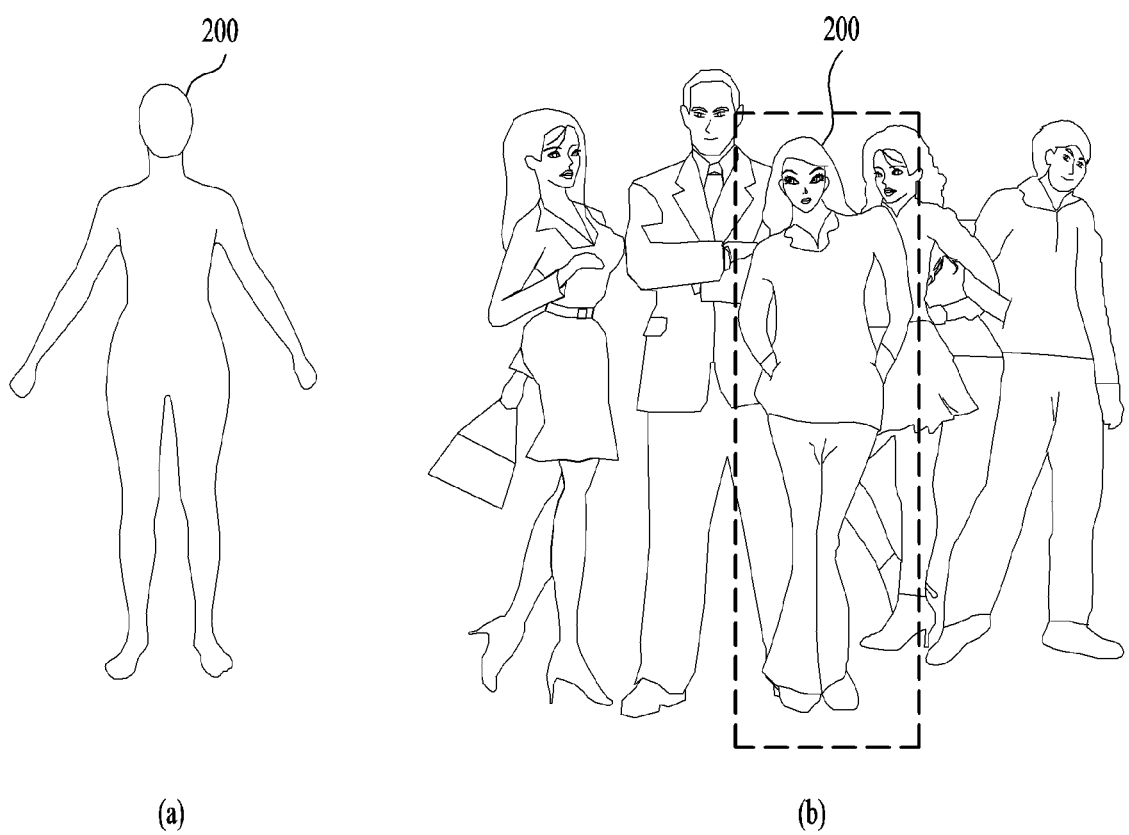
FIG. 9 illustrates a user's pose according to one embodiment of the present disclosure.

FIG. 9 illustrates a user's pose according to one embodiment of the present disclosure. FIG. 9 includes FIG. 9(a) and FIG. 9(b).

FIG. 9(a) illustrates a user's pose. Referring to FIG. 9(a), the controller 130 estimates the user's pose based on an ear image, a nose image, an eye image, a shoulder image, a tiptoe image and a hip image, which are included in the RGB image 200.

The controller 130 controls the camera 110 to automatically capture a second image, which includes the user's body image in front of the camera 110, if the user's pose is a first pose. In this case, the first pose may be a key pose for executing a measurement algorithm.

The key pose may be defined as follows. In this pose, the user looks at the camera while standing at attention, and spreads out his/her arms at a specific angle. In this case, the specific angle may be 30 degrees. The key pose may have various poses without being limited to one pose.

If the user takes a key pose, the camera captures a plurality of user front images. This is because that data area accumulated to lower an error rate than that of one image if the plurality of user front images are captured.

The key pose may be checked from a key point of a pose. For example, when the user stands in front of the camera, the key point may be ankles, elbows, ears, eyes, a nose, a neck, shoulders, hips, etc.

FIG. 9(b) illustrates a method for specifying a user whose body size will be measured if there are a plurality of users.

Referring to FIG. 9(b), the sensor module 140 senses a distance between the body measurement device 100 and a user.

If there are plurality of users, the controller 130 controls the sensor module 140 to sense a user 200 closest to the body measurement device 100 among the plurality of users, and if the user's pose is a first pose, controls the camera 110 to capture a second image that includes a body image of the user 200 in front of the camera 110.

If a plurality of second images are captured, the controller 130 independently measures a body size based on the second image. Therefore, in the present disclosure, it is advantageous that an error rate may be lowered.

Figure 10:
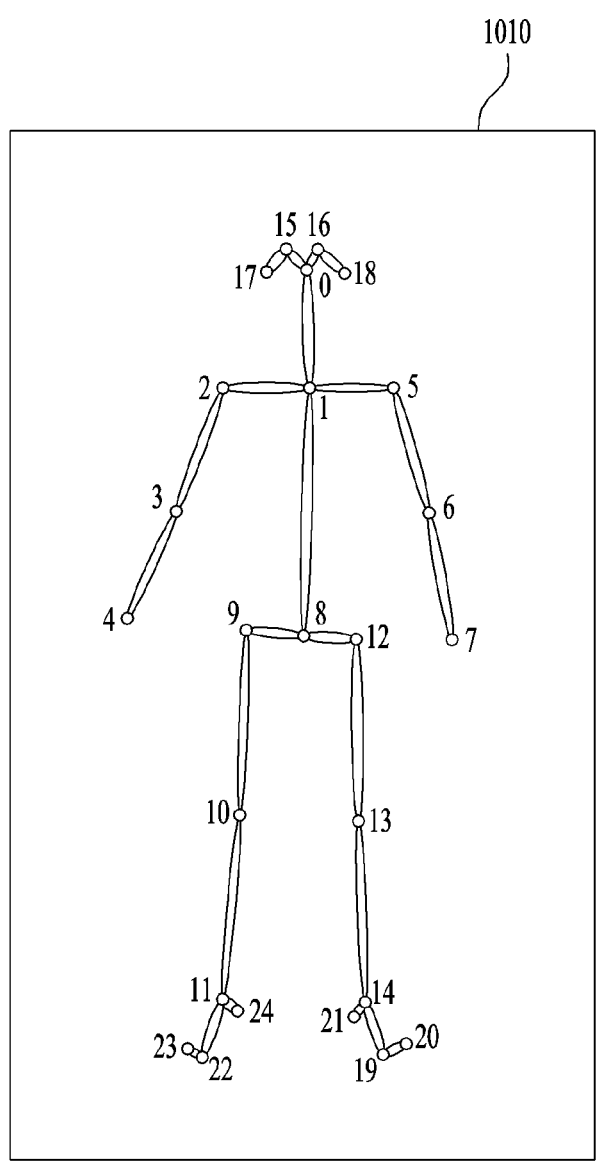
FIG. 10 illustrates a skeleton image according to one embodiment of the present disclosure.

FIG. 10 illustrates a skeleton image according to one embodiment of the present disclosure.

Referring to FIG. 10, the controller 130 extracts a skeleton image 1010 based on the first image, and estimates the user's pose based on the extracted skeleton image 1010.

The controller 130 may estimate the user's pose by using pose key points. The key points may be ears 17 and 18, eyes 15 and 16, a nose 0, a neck from 0 to 1, shoulders 2 and 5, elbows 3 and 6, and hips 9 and 12. The key points may be used to identify a key pose, and may also be used to estimate a body measurement size.

Figure 11:
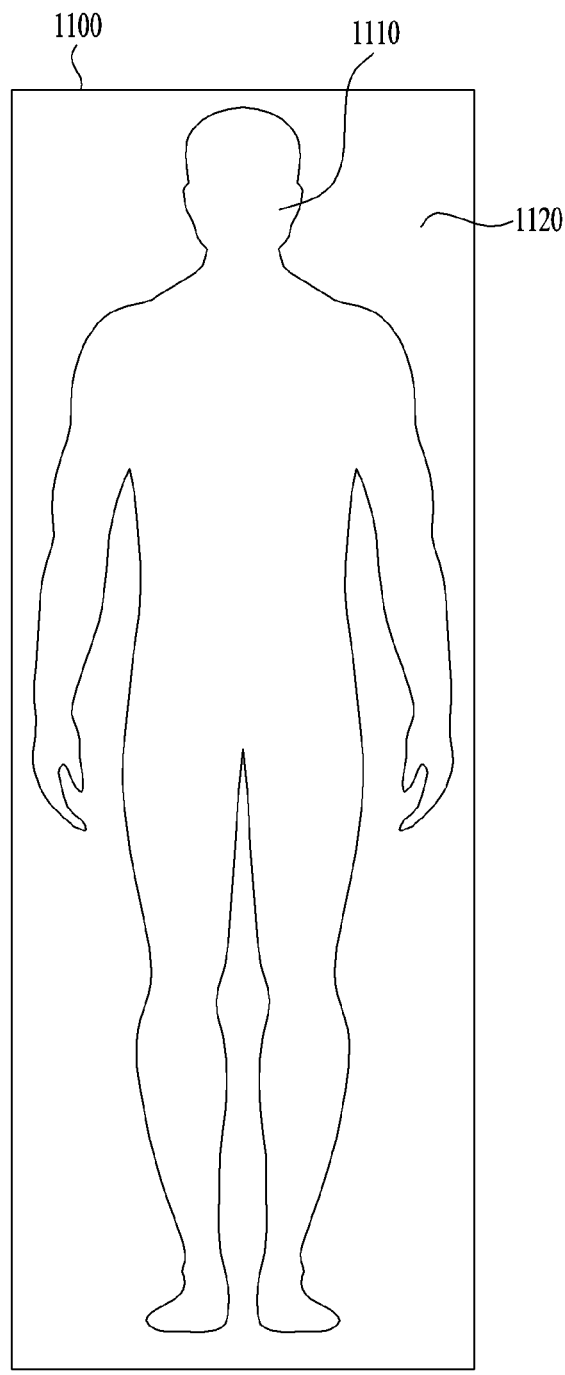
FIG. 11 illustrates that target segmentation is performed using an RGB image and a depth image in accordance with one embodiment of the present disclosure.

FIG. 11 illustrates that target segmentation is performed using an RGB image and a depth image in accordance with one embodiment of the present disclosure.

Referring to FIG. 11, target segmentation is executed using the RGB image and the depth image.

Target segmentation is executed as follows.

The controller 130 combines the RGB image with the depth image, and generates a body line image based on the combined RGB image and depth image. This will be described in more detail.

First of all, the controller 130 filters a depth map guided by the RGB image. The depth image includes a depth map.

The controller 130 executes trimap generation from the depth map. The controller performs matting for the depth map.

An output of target segmentation will be described.

The controller 130 generates a segmentation map of a target subject. Next, the controller 130 removes noise for the segmentation map, and performs a smooth treatment of an edge portion.

According to the present disclosure, the segmentation map may be used as a guide for body size measurement.

The target segmentation map will be described.

As shown in FIG. 11, the body line image may be segmented into a black area 1110 and a white area 1120. The controller 130 considers the black area 1110 as a front view and arranges the black area 1110 at the front, and considers the white area 1120 as a background and arranges the white area 1120 behind the black area 1120. In this image, the black area 1110 may mean a character in which a user is interested, and the white area 1120 may mean a background behind the character.

Therefore, the controller 130 generates the user's body line image 1100 based on the captured second image.

Figure 12:
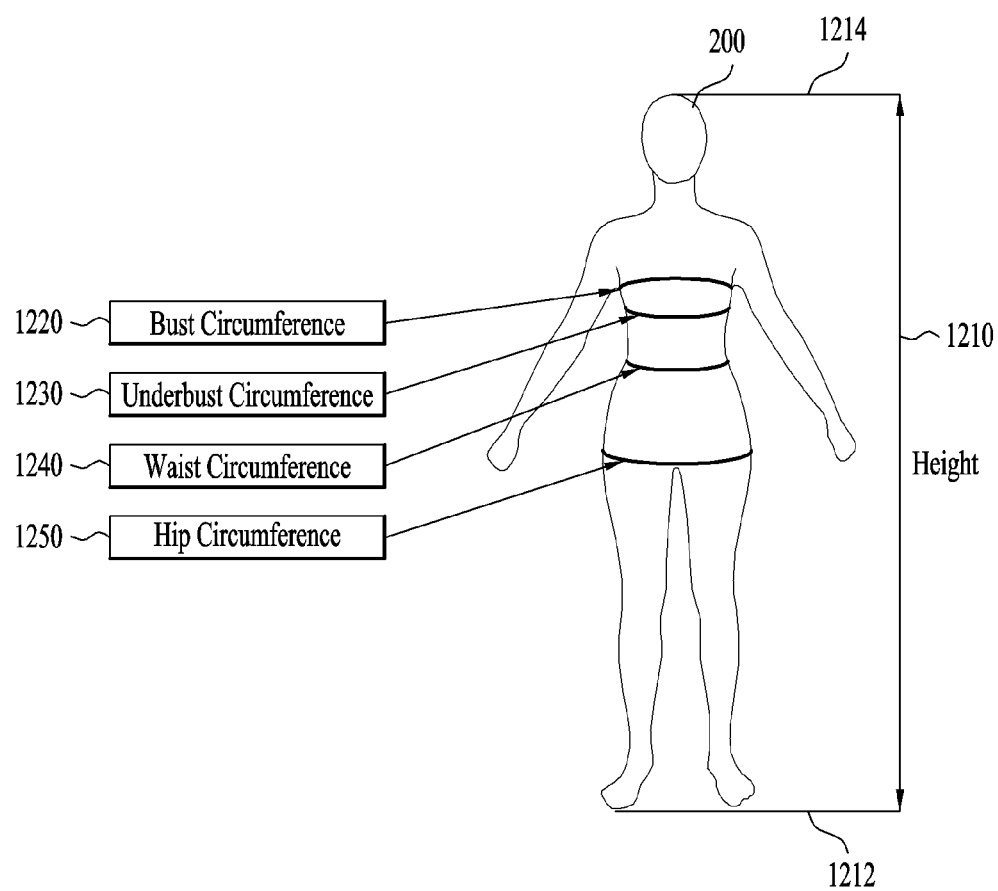
FIG. 12 illustrates a body size measurement target according to one embodiment of the present disclosure.

FIG. 12 illustrates a body size measurement target according to one embodiment of the present disclosure.

Referring to FIG. 12, a height 1210, a bust circumference length 1220, an underbust circumference length 1230, a waist circumference length 1240, and a hip circumference length 1250 may be measured based on the body line image 1200.

In detail, following data are required when a body size is measured. A depth map, a pose key point coordinate, and a body segmentation mask are required. The controller 130 generates a body line image 1200 based on the depth map, the pose key point coordinate and the body line mask.

Next, a body line measurement target is as follows. The controller 130 measures at least one of the user's height 1210, an arm length, a leg length, a bust circumference length 1220, a waist circumference length 1240, and a hip circumference length 1250.

Next, segmentation of body proportions and determination of a bust and a waist will be described.

The controller 130 segments the body line image 1200 into a predetermined ratio, determines a protruded portion of the body line image 1200 as a bust, and determines a recessed portion of the body line image 1200 as a waist.

For example, the height 1210 means a distance from the ground 1210 to a head end 1214.

A range between a neck and hips of the body line image 1200 is mainly used for body measurement. This portion may be considered as [0,1] in an upper body portion. The upper body portion includes a bust, a waist, and a hip portion. That is, when the body line image is divided into a predetermined ratio, a neck means 0, and the hip means 1.

The bust portion means a portion of [0.15 to 0.25] in the upper body.

The underbust portion means a portion of [0.35 to 0.45] in the upper body.

The waist portion means a portion of [0.65 to 0.75] in the upper body.

The hip portion means a portion of [0.95 to 1.00] in the upper body.

The above values are not fixed, and the controller 130 may set the values differently depending on the body line image with reference to the memory 150. The memory 150 includes various body line images, and stores a body proportion corresponding to each body line image.

Figure 13:
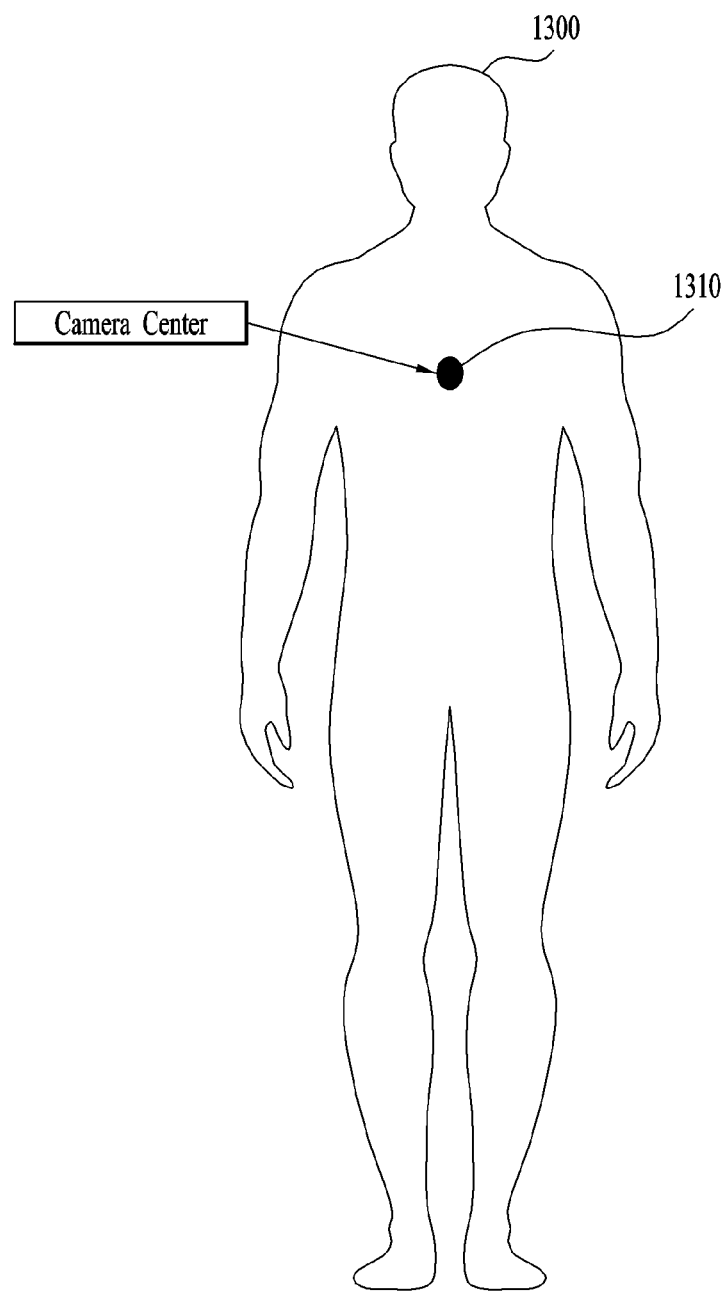
FIG. 13 illustrates that a user's height is measured in accordance with one embodiment of the present disclosure.

FIG. 13 illustrates that a user's height is measured in accordance with one embodiment of the present disclosure.

Referring to FIG. 13, a body line image 1300 includes a camera center 1310. The controller 130 may measure the user's height by using the camera center 1310.

The camera center 1310 is a distance from the ground to a camera lens, and means a camera height.

For example, if the camera height is 175 cm, the controller 130 controls the sensor module 140 to measure the camera height. The controller 130 measures the user's height based on the camera height.

If the camera height is lower than the user's height, the controller 130 determines a value obtained by adding a) the camera height to b) a distance between the camera and the user's head as the user's height.

For example, if the camera height is 175 cm and the distance between the camera and the user's head is 5 cm, the controller 130 determines 180 cm obtained by adding 175 cm to 5 cm as the user's height.

If the camera height is higher than the user's height, the controller 130 determines a value obtained by subtracting b) a distance between the camera and the user's head from a) the camera height as the user's height.

For example, if the camera height is 175 cm and the distance between the camera and the user's head is 5 cm, the controller 130 determines 170 cm obtained by subtracting 5 cm from 175 cm as the user's height.

Figure 14:
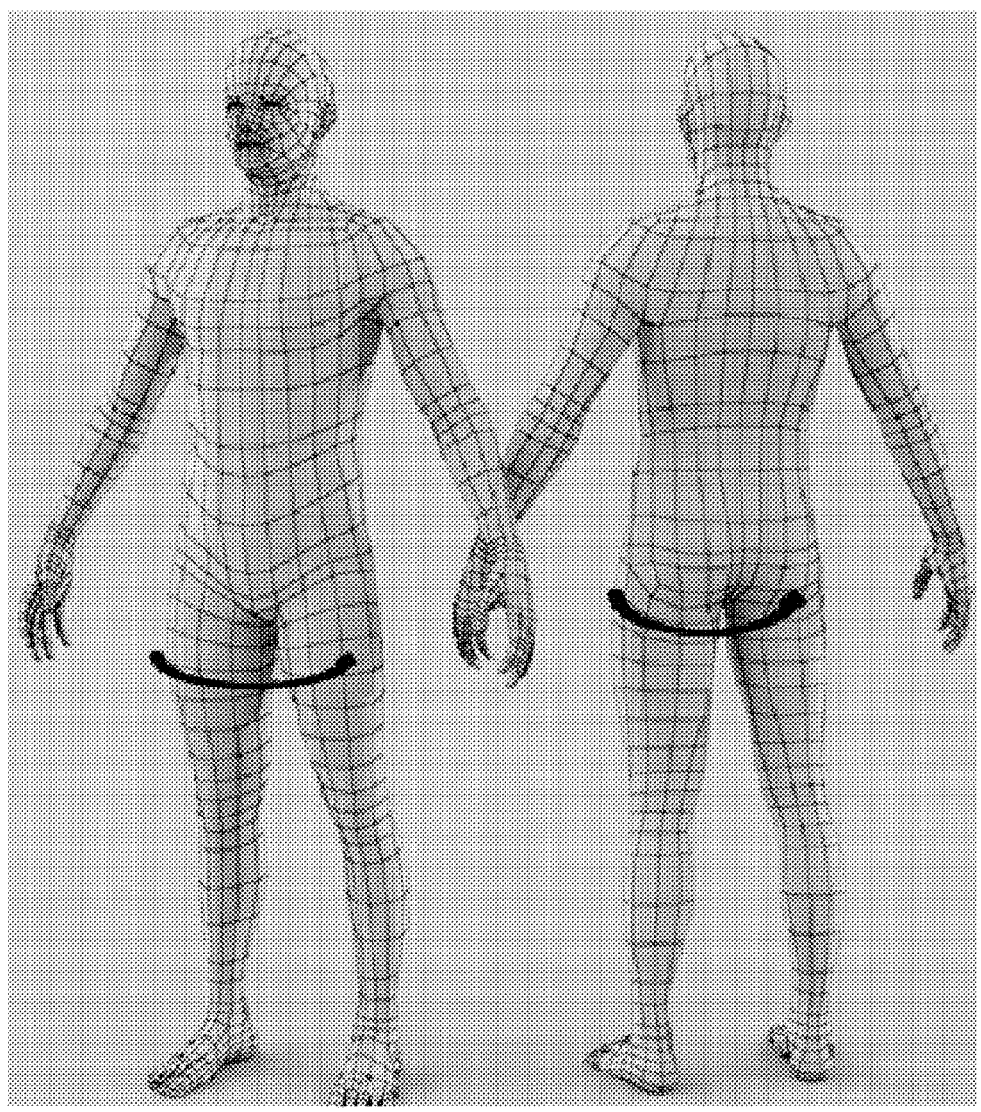
FIG. 14 illustrates two methods for measuring a user's waist circumference length in accordance with one embodiment of the present disclosure.

FIG. 14 illustrates two methods for measuring a user's waist circumference length in accordance with one embodiment of the present disclosure. FIG. 14 includes FIG. 14(a) and FIG. 14(b).

FIG. 14(a) illustrates that a user's front image is captured. FIG. 14(b) illustrates that a user's rear image is captured.

The first method is the case that both a front image and a rear image are captured. In this case, the controller 130 may most exactly measure a circumference length based on the depth map. Also, since a ratio of a body size and depth information may be known based on the skeleton image, the controller 130 may measure the circumference length more exactly.

The second method is the case that a front image is only captured. A rear circumference length may be obtained using an estimation method. That is, the rear circumference length is associated with a straight line length of the body. The rear circumference length may be obtained by multiplying a specific parameter by a straight line length based on experimental data.

This will be described later in detail with reference to FIGS. 15 and 16.

Figure 15:
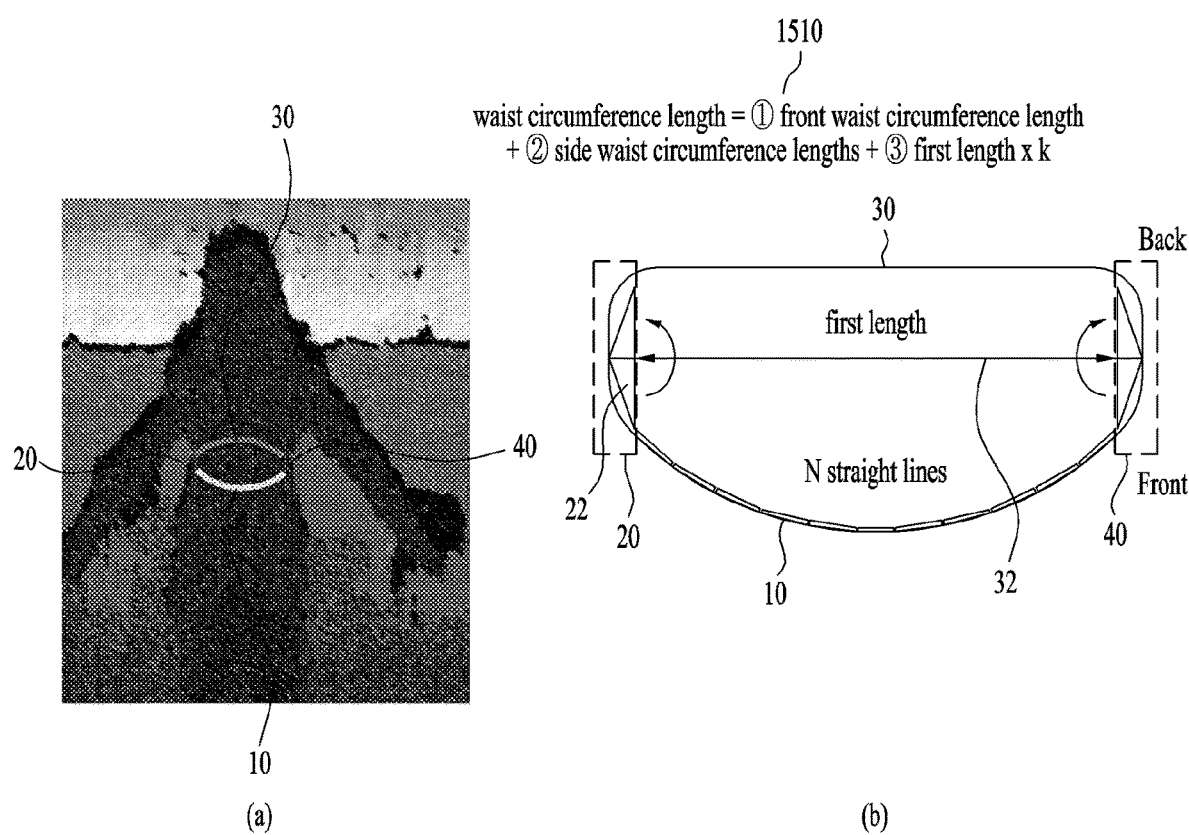
FIG. 15 illustrates that a waist circumference length is measured in accordance with one embodiment of the present disclosure.

FIG. 15 illustrates that a waist circumference length is measured in accordance with one embodiment of the present disclosure. FIG. 15 includes FIG. 15(a) and FIG. 15(b).

In the case of the present invention, only one example of measuring the waist circumference length will be described, but in the case of the chest circumference length and the hip circumference length can be measured in the same manner.

FIG. 15(a) illustrates a user's waist circumference length area in a full user body line image. FIG. 15(b) illustrates a user's waist circumference length area in detail.

Referring to FIG. 15(a), the waist circumference length 1510 is equal to front waist circumference length 10+side waist circumference lengths 20 and 40+rear waist circumference length 30.

As shown in FIG. 15(b), an enlarged image that includes the front waist circumference length 10, the side waist circumference lengths 20 and 40 and the rear waist circumference length 30 will be described.

In case of the front waist circumference length 10, the controller 130 obtains the front waist circumference length 10 by segmenting the front waist circumference into n straight lines and adding n straight line lengths.

The controller 130 uses data having noise of a predetermined range or more among data acquired from the depth camera for calculation of the side waist circumference length 20. The controller 130 uses data having noise less than a predetermined range for calculation of the front waist circumference length 10.

In the present disclosure, since the data having noise less than a predetermined range are explicit data, the data may be used for measurement of the front waist circumference length. Since the data having noise of a predetermined range or more are not explicit data, the data may be used for measurement of the side waist circumference length, whereby a body size may be measured more exactly.

The controller 130 obtains a length 22 of a long side by using a right-angled triangle, and obtains the left side waist circumference length 20 by multiplying the obtained length 22 of the long side two times.

The right side waist circumference length 40 is obtained equally to the left side waist circumference length 20.

According to the present disclosure, noise occurs in case of the depth camera, whereby a boundary line of a body is not exact. In this case, it is advantageous that the side circumference length may be predicted using a right-angled triangle.

The controller 130 extracts a first length 32 from the body line image and determines the rear waist circumference length 30 by multiplying a specific parameter by the extracted first length 32.

For example, the rear circumference length 30 is obtained using a first length×k parameter. In this case, the k parameter means experimental data based on actually measured data.

The k parameter is changed depending on a body portion. For example, the k parameter of the waist portion is smaller than the k parameter of the bust portion.

The first length 32 means a length when a start point and an end point of the front waist circumference length 10 are connected with each other by a straight line.

The controller 130 determines the front waist circumference length 10, the side waist circumference lengths 20 and 40 and the rear waist circumference length 30 based on the generated body line image, and measures the waist circumference length among the user's body sizes by combining the front waist circumference length 10, the side waist circumference lengths 20 and 40 and the rear waist circumference length 30.

According to the present disclosure, the bust circumference length and the hip circumference length may be measured in the same manner as the above method.

Figure 16:
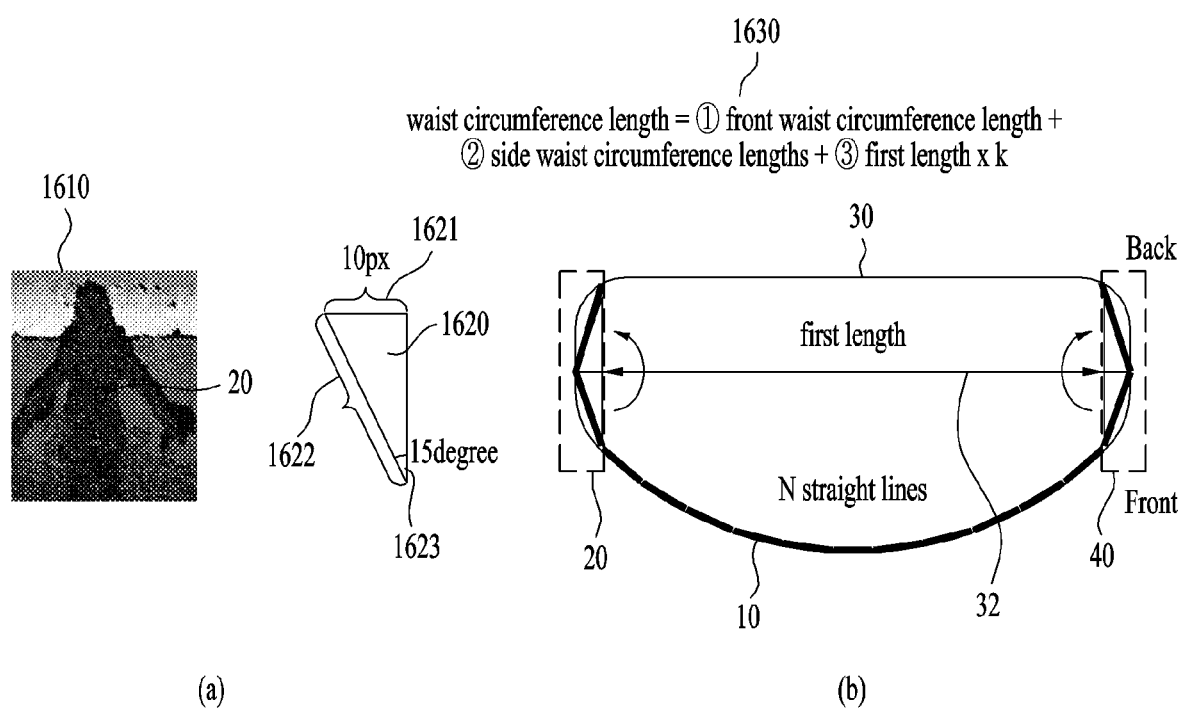
FIG. 16 illustrates that a front waist circumference length, a side waist circumference length, and a rear waist circumference length are measured in accordance with one embodiment of the present disclosure.

FIG. 16 illustrates that a front waist circumference length, a side waist circumference length, and a rear waist circumference length are measured in accordance with one embodiment of the present disclosure. FIG. 16 includes FIG. 16(a) and FIG. 16(b).

FIG. 16(a) illustrates a method for obtaining a side waist circumference length in detail. Referring to FIG. 16(a), the controller 130 the side waist circumference length based on a body line image 1610.

First of all, a description will be given based on that the side waist circumference length is obtained. The side waist circumference length is obtained using a right-angled triangle 1620. The right-angled triangle 1620 includes a first side 1621, a large side 1622 and a first angle 1623.

A key point is to know an actual length of the large side 1622 of the right-angled triangle 1620. First of all, the controller 130 uses data having noise of a predetermined range or more among data acquired from the depth camera for calculation of the side waist circumference length 20. That is, the side waist circumference length is determined based on noise.

For example, if noise is a predetermined range or more, the controller 130 obtains a length of the first side 1621. The length of the first side 1621 may be 10 pixels.

The controller 130 may estimate the first angle 1623 based on experimental data. For example, the first angle may be 15 degrees.

The controller 130 may calculate the actual length of the large side 1622 based on the first side 1621 and the first angle 1623. The actual length of the large side 1622 is obtained by multiplying a length (the number of pixels) of the large side by a pixel length per meter (PPM).

FIG. 16(b) illustrates a waist circumference length area in detail by cutting the user's waist. Referring to FIG. 16(b), the controller 130 obtains the side waist circumference lengths 20 and 40 based on the body line image 1610. The waist circumference length 1630 is equal to front waist circumference length 10+side waist circumference lengths 20 and 40+rear waist circumference length 30.

A method for obtaining the rear waist circumference length 30 will be described in more detail.

The controller 130 extracts a first length 32 from the body line image and determines the rear waist circumference length 30 by multiplying a specific parameter by the extracted first length 32.

For example, the rear circumference length 30 is obtained using a first length×k parameter. In this case, the k parameter means experimental data based on actually measured data. The first length 32 means a length when a start point and an end point of the front waist circumference length 10 are connected with each other by a straight line.

The rear waist circumference length 30 may be considered as a half of an oval circumference length. The oval circumference length is proportional to a length of a long axis. Also, the oval circumference length is proportional to a length of a short axis. A half of the rear waist circumference length 30 may be multiplication of the first length 32 and the k parameter. In this case, the k parameter is determined differently depending on a body portion. For example, the k parameter of the waist portion is smaller than the k parameter of the bust portion. Also, the k parameter is experimental data obtained based on the actually measured data.

FIG. 17 illustrates data of a user's actual height and a measured height according to one embodiment of the present disclosure.

Referring to FIG. 17, if a user is CHC, the user's actual height is 1.78 m. The actual height means a value measured using a tape measure.

A first experimental value becomes 1.78202 m.
A second experimental value becomes 1.77908 m.
A third experimental value becomes 1.76101 m.
A fourth experimental value becomes 1.79096 m.
A fifth experimental value becomes 1.79234 m.

In this way, measurement may be performed up to a tenth experimental value, and an average of errors from the first experimental value to the tenth experimental value becomes 0.015 m.

Even if the user is UEN, ZF, WJU, or PSO, measurement may be performed in the same way.

FIG. 18 illustrates data of a user's actual bust circumference length and a measured bust circumference length according to one embodiment of the present disclosure.

Referring to FIG. 18, if a user is CHC, the user's bust circumference length becomes 0.98 m. The actual bust circumference length means a value measured using a tape measure.

A first experimental value becomes 1.04009 m.
A second experimental value becomes 1.02241 m.
A third experimental value becomes 1.00679 m.
A fourth experimental value becomes 1.01789 m.
A fifth experimental value becomes 1.01635 m.

In this way, measurement may be performed up to a tenth experimental value, and an average of errors from the first experimental value to the tenth experimental value becomes 0.032 m.

Even if the user is UEN, ZF, WJU, or PSO, measurement may be performed in the same way.

FIG. 19 illustrates data of a user's actual underbust circumference length and a measured underbust circumference length according to one embodiment of the present disclosure.

Referring to FIG. 19, if a user is CHC, the user's underbust circumference length becomes 0.88 m. The actual underbust circumference length means a value measured using a tape measure.

A first experimental value becomes 0.959572 m.
A second experimental value becomes 0.960445 m.
A third experimental value becomes 0.885358 m.
A fourth experimental value becomes 0.869253 m.
A fifth experimental value becomes 0.903299 m.

In this way, measurement may performed up to a tenth experimental value, and an average of errors from the first experimental value to the tenth experimental value becomes 0.040 m.

Even if the user is UEN, ZF, WJU, or PSO, measurement may be performed in the same way.

FIG. 20 illustrates data of a user's actual waist circumference length and a measured waist circumference length according to one embodiment of the present disclosure.

Referring to FIG. 20, if a user is CHC, the user's waist circumference length becomes 0.92 m. The actual waist circumference length means a value measured using a tape measure.

A first experimental value becomes 0.985915 m.
A second experimental value becomes 0.939380 m.
A third experimental value becomes 0.929100 m.
A fourth experimental value becomes 0.910563 m.
A fifth experimental value becomes 0.914214 m.

In this way, measurement may be performed up to a tenth experimental value, and an average of errors from the first experimental value to the tenth experimental value becomes 0.025 m.

Even if the user is UEN, ZF, WJU, or PSO, measurement may be performed in the same way.

FIG. 21 illustrates data of a user's actual hip circumference length and a measured hip circumference length according to one embodiment of the present disclosure.

Referring to FIG. 21, if a user is CHC, the user's hip circumference length becomes 0.99 m. The actual hip circumference length means a value measured using a tape measure.

A first experimental value becomes 1.09757 m.
A second experimental value becomes 1.06528 m.
A third experimental value becomes 1.06060 m.
A fourth experimental value becomes 1.04748 m.
A fifth experimental value becomes 1.04226 m.

In this way, measurement may performed up to a tenth experimental value, and an average of errors from the first experimental value to the tenth experimental value becomes 0.039 m.

Even if the user is UEN, ZF, WJU, or PSO, measurement may be performed in the same way.

FIG. 22 illustrates data of an error and exactness of a user's body size measurement data according to one embodiment of the present disclosure.

Referring to FIG. 22, an error rate will be described.
In case of a height, an error rate becomes 0.6%.
In case of a bust circumference length, an error rate becomes 6.1%.
In case of an underbust circumference length, an error rate becomes 4.9%.
In case of a waist circumference length, an error rate becomes 2.3%.
In case of a hip circumference length, an error rate becomes 2.0%.

Exactness will be described. Exactness means a value obtained by subtracting an error rate from 100%.
In case of a height, exactness becomes 99.4%.
In case of a bust circumference length, exactness becomes 93.9%.
In case of an underbust circumference length, exactness becomes 95.1%.
In case of a waist circumference length, exactness becomes 97.7%.
In case of a hip circumference length, exactness becomes 98.0%.

FIG. 23 illustrates data of an error and exactness of a user's body size measurement data according to one embodiment of the present disclosure.

Referring to FIG. 23, if a user is UEK, the user's actual height becomes 1.53 m. The actual key means a value measured using a tape measure.

A first experimental value becomes 1.52192 m.
A second experimental value becomes 1.53040 m.
A third experimental value becomes 1.54128 m.
A fourth experimental value becomes 1.53899 m.
A fifth experimental value becomes 1.54272 m.

An average of errors from the first experimental value to the fifth experimental value becomes 0.00933063 m.

Even if the user is KBR, ZU, or CHC, measurement may be performed in the same way.

Next, an error rate will be described.
In case of a height, an error rate becomes 0.2%.
In case of a shoulder length, an error rate becomes 1.6%.
In case of an arm length, an error rate becomes 2.5%.

Exactness will be described. Exactness means a value obtained by subtracting an error rate from 100%.
In case of a height, exactness becomes 99.8%.
In case of a shoulder length, exactness becomes 98.4%.
In case of an arm length, exactness becomes 97.5%.

Figure 24:
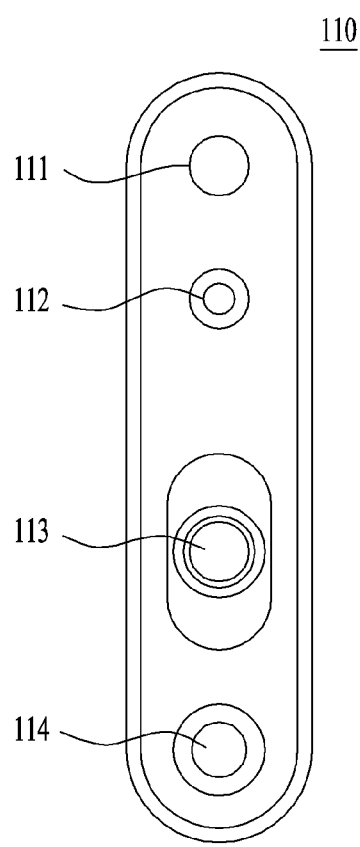
FIG. 24 illustrates a structure of a camera of a body measurement device according to one embodiment of the present disclosure.

FIG. 24 illustrates a structure of a TOF camera of a body measurement device according to one embodiment of the present disclosure.

Referring to FIG. 24, the TOF camera 110 includes an RGB camera 111, a first IR camera 112, an IR light 113, and a second IR camera 114.

In this case, TOF the camera 110 is vertically provided in the body measurement device 100. The camera 110 should be provided vertically to generate a depth image with more stereoscopic effect when capturing a person image.

If the TOF camera 110 is used, map type 3D depth information may be output, and noise based on a light change is less generated than a stereo vision technology and is not the result based on image processing so that it is advantageous that textureless or occlusion is not generated.

FIG. 25 illustrates a use example of a body measurement device according to one embodiment of the present disclosure. FIG. 25 includes FIG. 25(a) and FIG. 25(b).

FIG. 25(a) illustrates that the body measurement device 100 is provided in a stylus, and a user 200 stands in front of the body measurement device 100. As shown in FIG. 25(a), the camera 110 of the body measurement device 100 measures a body size by capturing the user's whole body image.

FIG. 25(b) illustrates that the body measurement device 100 is provided in a tailor bot in a clothes store and the user 200 stands in front of the body measurement device 100. Referring to FIG. 25(b), the camera 110 of the body measurement device 100 measures a body size of the user by capturing the user's upper body or whole body image.

The tailor bot is a guide robot for recommending clothes for the user 200 and executing virtual fitting, and may measure a body size and perform virtual fitting by using an avatar corresponding to a user on the screen.

FIG. 26 illustrates an execution screen of a body measurement device according to one embodiment of the present disclosure. FIG. 26 includes FIG. 26(a) and FIG. 26(b).

FIG. 26(a) illustrates an execution screen of the body measurement device. Referring to FIG. 26(a), if the body measurement device 100 is executed, the controller 130 displays the current time, Jan. 14, 2019, 03:45, PM, and an important meeting schedule.

FIG. 26(b) illustrates that a procedure of executing a body measurement process is displayed when a user stands in front of the body measurement device 100.

If the user stands in front of the body measurement device 100, the controller 130 displays a text 2620 that includes a content indicating that a user stands straight and spreads his/her arms. Also, the controller 130 displays an image 2430 indicating the procedure of executing the body measurement process, for example, 64%. In this case, 0% means that the body measurement process starts, and 100% means that the body measurement process is completed.

Figure 27:
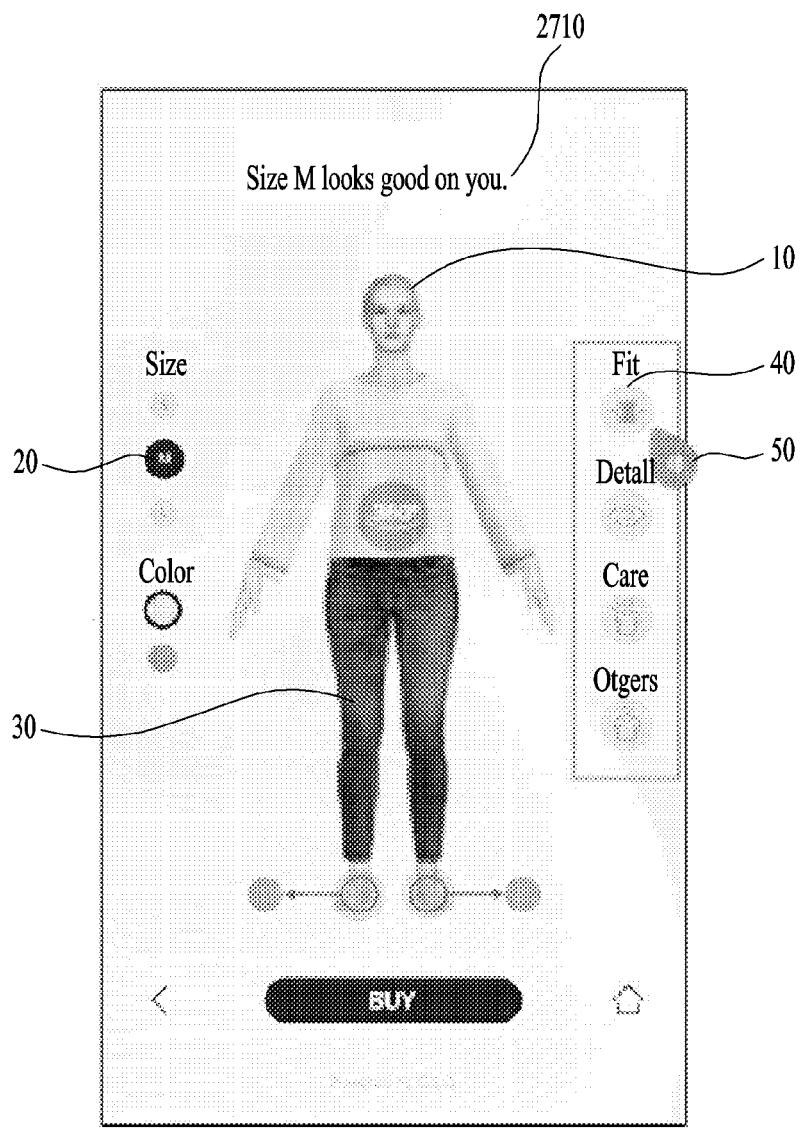
FIG. 27 illustrates an execution screen of a body measurement device according to one embodiment of the present disclosure.

FIG. 27 illustrates an execution screen of a body measurement device according to one embodiment of the present disclosure.

Referring to FIG. 27, the controller 130 displays an avatar 10 having the same body size as the user's body size on the screen.

For example, the user's body size includes a height of 172 cm, a bust circumference length of 101 cm, a waist circumference length of 94 cm, and a hip circumference length of 102 cm. In this case, clothes may be pants.

The controller 130 determines the most suitable clothes size based on the user's body size, and displays a text 2710 recommending clothes of M size for the user.

The size may be L, M and S, and if the user selects a specific size icon 20, the controller 130 displays an avatar 10 who wears clothes corresponding to the size icon 20 selected by the user. In this case, the clothes may be pants.

If an input 50 for selecting a fitting icon 40 is received from the user, the controller 130 displays an image indicating that the user wears pants. This will be described later with reference to FIG. 28.

Figure 28:
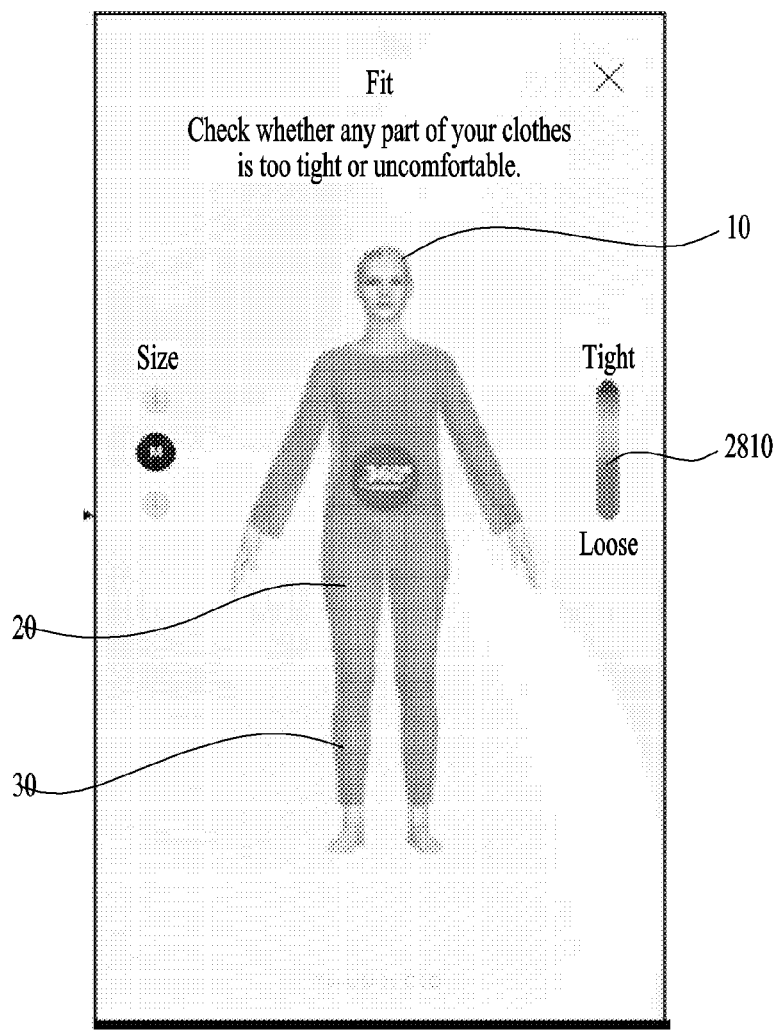
FIG. 28 illustrates an execution screen of a body measurement device according to one embodiment of the present disclosure.

FIG. 28 illustrates an execution screen of a body measurement device according to one embodiment of the present disclosure.

FIG. 28 illustrates a wearing state when a user wears pants of a specific size. The controller 130 displays a progressive bar 2810 indicating a wearing state. For example, the specific size may be M.

The progressive bar 2810 may be changed from a first color to a second color, wherein the first color means that clothes worn by the user are tight for the user, and the second color means that clothes worn by the user are loose for the user. A color change from the first color to the second color may be changed to a gradation effect.

When a user avatar 10 wears pants, the controller 130 displays a graphic image 20 indicating a wearing state per body portion on the avatar image 10. The graphic image 20 may be displayed differently depending on the wearing state per body portion.

For example, when the user avatar 10 wears pants, the controller 130 may display the graphic image 20, which includes a color meaning loose, on an upper portion of the pants, and may display a graphic image 30, which includes a color meaning tight, on a lower portion of the pants.

According to the present disclosure, when the user avatar 10 wears clothes of a specific size, the controller 130 displays a graphic image indicating a wearing state per body portion. Therefore, since the user may intuitively know whether clothes are tight or loose even though the user does not wear the clothes, user convenience may be improved.

According to one embodiment of the present disclosure, if the user takes a specific pose, the user's image is captured. After the RGB image and the depth image are combined with each other, the user's body line image may be generated from the captured image, and the user's body size may be measured based on the generated body line image. Therefore, the user's image may be captured by a simple operation and an exact body size may be measured, whereby user convenience may be improved.

According to another embodiment of the present disclosure, a skeleton image is extracted from the captured image, and the skeleton image, the RGB image and the depth image may be combined with one another to generate the user's body line image. Therefore, the user's body size may be measured more exactly, whereby user convenience may be improved.

According to still another embodiment of the present disclosure, a first length may be extracted from a body line image, and a specific parameter may be multiplied by the first length to determine a rear waist circumference length. Therefore, a waist circumference length which is invisible from a front image may exactly be measured, whereby user convenience may be improved.

The body measurement device and the method for controlling the same according to the present disclosure are not limited to the aforementioned embodiments, and all or some of the aforementioned embodiments may selectively be configured in combination so that various modifications may be made in the aforementioned embodiments.

Meanwhile, the method according to the present specification may be implemented as code that can be written on a processor-readable recording medium and thus read by a processor provided in a network device. The processor-readable recording medium may be any type of recording device in which data are stored in a processor-readable manner. The processor-readable recording medium may include, for example, read only memory (ROM), random access memory (RAM), compact disc read only memory (CD-ROM), magnetic tape, a floppy disk, and an optical data storage device, and may be implemented in the form of a carrier wave transmitted over the Internet. In addition, the processor-readable recording medium may be distributed over a plurality of computer systems connected to a network such that processor-readable code is written thereto and executed therefrom in a decentralized manner.

In addition, it will be apparent that, although the preferred embodiments have been shown and described above, the present specification is not limited to the above-described specific embodiments, and various modifications and variations can be made by those skilled in the art to which the present disclosure pertains without departing from the gist of the appended claims. Thus, it is intended that the modifications and variations should not be understood independently of the technical spirit or prospect of the present specification.

Various embodiments have been described in the best mode for carrying out the invention.

The present disclosure is used in a series of body measurement device-related fields in which an RGB image and a depth image are combined with each other to generate a user's body line image, and a body size of the user is measured based on the generated body line image.

Those skilled in the art will appreciate that the present disclosure may be carried out in other specific ways than those set forth herein without departing from the spirit and essential characteristics of the present disclosure. Therefore, the scope of the invention should be determined by the appended claims and their legal equivalents, rather than by the above description, and all changes that fall within the meaning and equivalency range of the appended claims are intended to be embraced therein.

What is claimed is:

1. A body measurement device comprising:
a TOF camera configured to capture a first image that includes an RGB image and a depth image;
a display configured to display a graphic image; and
a controller configured to:
estimate a user's pose based on the first image,
control the camera to automatically capture a second image, which includes the user's body image in front of the TOF camera,
when the user's pose is a first pose, generate the user's body line image based on the captured second image,
measure the user's body size based on the generated body line image; and
control the display to display the user's body size.

2. The body measurement device of claim 1, wherein the controller is further configured to:
extract a skeleton image based on the first image, and
estimate the user's pose based on the extracted skeleton image.

3. The body measurement device of claim 1, wherein the controller is further configured to:
extract a skeleton image based on the second image, and
generate the user's body line image by combining the extracted skeleton image, an RGB image and a depth image with one another,
wherein the second image includes the RGB image and the depth image.

4. The body measurement device of claim 1, wherein the controller is further configured to estimate the user's pose based on an ear image, a nose image, an eye image, a shoulder image, a tiptoe image, and a hip image, which are included in the RGB image.

5. The body measurement device of claim 1, further comprising a sensor module configured to sense a distance with a user,
wherein the controller is further configured to:
control the sensor module to sense the user closest to the body measurement device among a plurality of users when there are the plurality of users, and
control the TOF camera to capture a second image, which includes the user's body image in front of the TOF camera, when the user's pose is the first pose.

6. The body measurement device of claim 1, wherein the controller is further configured to measure at least one of the user's height, arm length, leg length, bust circumference, waist circumference, and hip circumference based on the generated body line image.

7. The body measurement device of claim 1, wherein the controller is further configured to:
divide the body line image into a predetermined ratio,
determine a protruded portion in the body line image as a bust, and
determine a recessed portion in the body line image as a waist.

8. The body measurement device of claim 1, wherein the controller is further configured to:
determine the user's front waist circumference length, side waist circumference lengths and rear waist circumference length based on the generated body line image, and
measure the user's body size by combining the front waist circumference length, the side waist circumference lengths and the rear waist circumference length.

9. The body measurement device of claim 8, wherein the controller is further configured to:
extract a first length from the body line image, and
determine the rear waist circumference length by multiplying a specific parameter by the extracted first length.

10. The body measurement device of claim 1, wherein the TOF camera includes an RGB camera, a first IR camera, and a second IR camera, and
wherein the TOF camera is vertically provided in the body measurement device.

11. A method for controlling a body measurement device, the method comprising:
- capturing a first image that includes an RGB image and a depth image, via a TOF camera;
- estimating a user's pose based on the first image;
- controlling the TOF camera to capture a second image, which includes the user's body image in front of the TOF camera, when the user's pose is a first pose;
- generating the user's body line image based on the captured second image;
- measuring the user's body size based on the generated body line image; and
- controlling a display to display the user's body size.

12. The method of claim 11, further comprising;
- extracting a skeleton image based on the first image; and
- estimating the user's pose based on the extracted skeleton image.

13. The method of claim 11, further comprising:
- extracting a skeleton image based on the second image; and
- generating the user's body line image by combining the extracted skeleton image, an RGB image and a depth image with one another,
- wherein the second image includes the RGB image and the depth image.

14. The method of claim 11, further comprising estimating the user's pose based on an ear image, a nose image, an eye image, a shoulder image, a tiptoe image, and a hip image, which are included in the RGB image.

15. The method of claim 11, further comprising:
- sensing, via a sensor module, a user closest to the body measurement device among a plurality of users when there are the plurality of users; and
- controlling the camera to capture a second image, which includes the user's body image in front of the TOF camera, when the user's pose is the first pose.

16. The method of claim 11, further comprising measuring at least one of the user's height, arm length, leg length, bust circumference, waist circumference, and hip circumference based on the generated body line image.

17. The method of claim 11, further comprising:
- dividing the body line image into a predetermined ratio;
- determining a protruded portion in the body line image as a bust; and
- determining a recessed portion in the body line image as a waist.

18. The method of claim 11, further comprising:
- determining the user's front waist circumference length, side waist circumference lengths and rear waist circumference length based on the generated body line image; and
- measuring the user's body size by combining the front waist circumference length, the side waist circumference lengths and the rear waist circumference length.

19. The method of claim 18, further comprising:
- extracting a first length from the body line image; and
- determining the rear waist circumference length by multiplying a specific parameter by the extracted first length.

20. The method of claim 11, wherein the TOF camera includes an RGB camera, a first IR camera, and a second IR camera, and
- wherein the TOF camera is vertically provided in the body measurement device.

* * * * *